United States Patent
Asami et al.

(10) Patent No.: US 8,741,807 B2
(45) Date of Patent: Jun. 3, 2014

(54) PLANT ACTIVATOR

(75) Inventors: Tadao Asami, Tokyo (JP); Masashi Hikosaka, Hyogo (JP); Masaki Mori, Ibaraki (JP); Satoru Maeda, Ibaraki (JP); Fumio Matsuda, Hyogo (JP); Kazuki Saito, Chiba (JP)

(73) Assignees: The University of Tokyo, Tokyo (JP); National Institute of Agrobiological Sciences, Ibaraki (JP); Riken, Saitama (JP)

( * ) Notice: Subject to any disclaimer, the term of this patent is extended or adjusted under 35 U.S.C. 154(b) by 0 days.

(21) Appl. No.: 13/402,947

(22) Filed: Feb. 23, 2012

(65) Prior Publication Data

US 2013/0172189 A1    Jul. 4, 2013

Related U.S. Application Data

(60) Provisional application No. 61/541,496, filed on Sep. 30, 2011.

(30) Foreign Application Priority Data

Feb. 24, 2011 (JP) .................................. 2011-038545

(51) Int. Cl.
| | | |
|---|---|---|
| A01N 25/32 | (2006.01) | |
| A01N 31/02 | (2006.01) | |
| A01N 33/04 | (2006.01) | |
| C07C 211/14 | (2006.01) | |
| C07C 215/14 | (2006.01) | |
| C07C 217/04 | (2006.01) | |
| C07C 217/42 | (2006.01) | |
| C07C 223/02 | (2006.01) | |

(52) U.S. Cl.
USPC ............ 504/112; 504/118; 504/189; 504/326; 504/334; 504/339; 514/579; 514/663; 514/674; 562/123; 562/152; 562/159; 562/160; 562/192

(58) Field of Classification Search
USPC ......... 504/112, 118, 189, 326, 334, 335, 339; 514/579, 663, 674; 562/123, 152, 159, 562/160, 192, 197
See application file for complete search history.

(56) References Cited

PUBLICATIONS

Yoda et al., "Induction of Hypersensitive Cell Death by Hydrogen Peroxide Produced through Polyamine Degradation in Tobacco Plants," 2003, Plant Physiology, 132:1973-1981.*
Yoda et al., "Polyamines as a common source of hydrogen peroxide in host- and nonhost-hypersensitive response during pathogen infection," 2009, Plant Mol. Biol., 710:103-112.*
Perez-Amador et al., "N4-Hexanoylspermidine, a New Polyamine-Related Compound That Accumulates during Ovary and Petal Senescence in Pea," 1996, Plant Physiol., 110:1177-1186.*
Mori et al., "Isolation and molecular characterization of a Spotted leaf 18 mutant by modified activation-tagging in rice", Plant Mol. Biol., 2007, pp. 847-860.

(Continued)

*Primary Examiner* — Jane C Oswecki
(74) *Attorney, Agent, or Firm* — Greenblum & Bernstein, P.L.C.

(57) ABSTRACT

A compound useful as a plant activator for activating an endogenous defense system of a plant to control disease damage is provided. A compound represented by the formula: $(R^3)NH-(CH_2)_4-N(R^1)-(CH_2)_3-NH(R^2)$ (one of $R^1$ and $R^2$ represents a linear $C_{6-18}$ alkanoyl group or alkenoyl group, the other represents hydrogen atom or a protective group of amino group; and $R^3$ represents hydrogen atom or a protective group of amino group).

9 Claims, 15 Drawing Sheets

(56) References Cited

PUBLICATIONS

Matsuda et al., "Functional estimation of rice OsAT1 gene based on the metabolic profiling analysis", Apr. 1, 2008, pp. 1.

Yoda et al., "Polyamines as a common source of hydrogen peroxide in host- and nonhost hypersensitive response during pathogen infection", Plant Mol. Biol., 2009, pp. 103-112.

Yoda et al., "Induction of Hypersensitive Cell Death by Hydrogen Peroxide Produced through Polyamine Degradation in Tobacco Plants", Plant Physiol., 2003, pp. 1973-1981.

Perez-Amador et al., "N4-Hexanoylspermidine, a New Polyamine-Related Compound That Accumulates during Ovary and Petal Senescence in Pea", Plant Physiol., 1996, pp. 1177-1186.

Luo et al., "A Novel Polyamine Acyltransferase Responsible for the Accumulation of Spermidine Conjugates in *Arabidopsis* Seed", The Plant Cell, 2009, pp. 318-333.

Fixon-Owoo et al., "Preparation and biological assessment of hydroxycinnamic acid amides of polyamines", Phytochemistry, 2003, pp. 315-334.

Bienz et al., "Polyamine alkaloids", Nat. Prod. Rep., 2005, pp. 647-658.

\* cited by examiner (A)

(B)

PLANT ACTIVATOR

TECHNICAL FIELD

The present invention relates to a plant activator which activates an endogenous defense system possessed by a plant to control disease damage thereof.

BACKGROUND ART

Crop damage due to disease is a significant cause of yield reduction, and as a countermeasure, crop protection is widely performed with agricultural chemicals such as fungicides and disease damage resistant varieties used in combination. However, there arises a serious problem that use of fungicides induces pathogenic microbes of plant diseases to have resistance against the fungicides. Although methods of using a plurality of fungicides having different mode of action in combination have been widely employed to solve the aforementioned problem, influences on the environment are concerned in the current strategy mainly based on the use of fungicides. Therefore, development of a novel method for controlling disease damage with consideration for the environment has been desired.

Under the circumstances as described above, plant activators which activate endogenous defense systems of plants to control disease damage of the plants (also called as plant vitalizers or disease damage resistance inducers) have been focused. The plant activators have no problem of inducing resistance in pathogenic microbes of plant diseases, and have less direct influences on the ecosystem itself, and therefore they are expected to be crop protection means that can significantly reduce the stress on the environment.

When plants perceive invasion of pathogenic microbes, they operate a defense mechanism called hypersensitive cell death, which induces spontaneous death of cells surrounding an infection site to form characteristic necrotic lesions and thereby prevent spread of infection. Although it is expected that elucidation of the process of establishing the hypersensitive cell death leads to understanding of an activation mechanism of disease damage resistance response in plants, the details thereof have not yet been elucidated.

The acyl transferase (OsAT1) gene has recently been identified as a gene involved in biosynthesis of substances in rice plant (Plant Mol. Biol., 63, pp. 847-860, 2007), and it has been reported that, in an OsAT1 high expression strain, expression induction of acquired systemic resistance marker genes PBZ1 and PR1, accumulation of rice plant phytoalexins, and resistance to rice blast are improved (The 33rd Convention of the Pesticide Science Society of Japan, Matsuda et al., Subject number: C312, Apr. 1, 2008). Under assumption that a product resulting from a reaction catalyzed by OsAT1 might trigger the induction of a series of disease damage resistance responses, Matsuda et al. found six components, of which contents always increased when OsAT1 was overexpressed, and reported that one (UK1) of the compounds was estimated to be an amide compound formed by an amino-containing compound and hydroxylauric acid on the basis of MS/MS analysis. However, the chemical structure of this substance has not been fully identified.

Spermidine is one of typical polyamines and known to be involved in induction of cell death such as hypersensitive response (HR) through production of hydrogen peroxide (Plant Mol. Biol., 70(1-2), pp. 103-112, 2009; Plant Physiol., 132(4), pp. 1973-1981, 2003). Further, since reactive oxygen species such as hydrogen peroxide and nitrogen monoxide, which are important signals for HR, are also important signals for other disease damage resistance responses, they are considered to be possibly involved in disease damage resistance other than HR.

As for actions of spermidine derivatives on plants, it is so far known that $^4$N-hexanoylspermidine is accumulated in plant body of *Pisum sativum* with senility thereof (Plant Physiol., 10(4), 1177-1186, 1996). However, induction of resistance to plant diseases by spermidine derivatives has not been reported. Several cinnamic acid derivatives of spermidine are known, and a disease damage-inductive hydroxycinnamic acid derivative existing in *Arabidopsis thaliana* (The Plant Cell, 21, pp. 318-333, 2009), a hydroxycinnamic acid derivative having insecticidal activity or the like (Phytochemistry, 63, pp. 315-334, 2003), and polyamine derivatives (Nat. Prod. Rep., 22, pp. 647-658, 2005) have been reported. However, actions of these spermidine cinnamic acid derivatives for inducing resistance to disease damage of plants have not been reported.

PRIOR ART REFERENCES

Non-Patent Documents

[Non-patent document 1] Plant Mol. Biol., 63, pp. 847-860, 2007
[Non-patent document 2] The 33rd Convention of the Pesticide Science Society of Japan, Subject number: C312, Apr. 1, 2008
[Non-patent document 3] Plant Mol. Biol., 70 (1-2), pp. 103-112, 2009
[Non-patent document 4] Plant Physiol., 132(4), pp. 1973-1981, 2003
[Non-patent document 5] Plant Physiol., 10(4), pp. 1177-1186, 1996
[Non-patent document 6] The Plant Cell, 21, pp. 318-333, 2009
[Non-patent Document 7] Phytochemistry, 63, pp. 315-334, 2003
[Non-patent document 8] Nat. Prod. Rep., 22, pp. 647-658, 2005

SUMMARY OF THE INVENTION

Object to be Achieved by the Invention

An object of the present invention is to provide a compound useful as a plant activator for activating an endogenous defense system of a plant to control disease damage.

Means for Achieving the Object

The inventors of the present invention conducted various researches to achieve the aforementioned object, and as a result, found that acylated spermidine derivatives successfully induced a disease damage resistance response in rice plant, and were usable as a plant activator. They also found that such spermidine derivatives having a linear alkanoyl group as the acyl group had a potent action as a plant activator, and such compounds in which hydroxyl group was introduced into the linear alkanoyl group had still more potent action as a plant activator. The present invention was accomplished on the basis of the aforementioned findings.

The present invention thus provides a compound represented by the following general formula (I):

(In the formula, one of $R^1$ and $R^2$ represents a linear alkanoyl group having 6 to 18 carbon atoms or a linear alkenoyl group having 6 to 18 carbon atoms (the linear alkanoyl group and the linear alkenoyl group may have 1 to 3 hydroxyl groups, and/or 1 to 3 alkyl groups having 1 to 4 carbon atoms), the other represents hydrogen atom or a protective group of amino group; and $R^3$ represents hydrogen atom or a protective group of amino group), or a salt thereof.

According to preferred embodiments of the aforementioned invention, there are provided the aforementioned compound or a salt thereof, wherein one of $R^1$ and $R^2$ is a linear alkanoyl group having 8 to 13 carbon atoms or a linear alkenoyl group having 8 to 13 carbon atoms (the linear alkanoyl group and the linear alkenoyl group may have 1 to 3 hydroxyl groups), the other is hydrogen atom or a protective group of amino group, and $R^3$ is hydrogen atom or a protective group of amino group; the aforementioned compound or a salt thereof, wherein one of $R^1$ and $R^2$ is a linear alkanoyl group having 8 to 13 carbon atoms (the linear alkanoyl group may have 1 to 3 hydroxyl groups), the other is hydrogen atom or a protective group of amino group, and $R^3$ is hydrogen atom or a protective group of amino group; the aforementioned compound or a salt thereof, wherein the linear alkanoyl group is a linear alkanoyl group having 9 to 12 carbon atoms (the linear alkanoyl group may have 1 or 2 hydroxyl groups); the aforementioned compound or a salt thereof, wherein the linear alkanoyl group is a linear alkanoyl group having 9 to 12 carbon atoms (the linear alkanoyl group has one hydroxyl group); and the aforementioned compound or a salt thereof, wherein the linear alkanoyl group is a linear alkanoyl group having 9 to 12 carbon atoms (the linear alkanoyl group has one hydroxyl group at the end). As the protective group of amino group, for example, a linear or branched alkanoyl group having 2 to 6 carbon atoms, a linear or branched alkoxycarbonyl group having 2 to 6 carbon atoms, and the like are preferred.

From another aspect, the present invention provides a plant activator comprising a compound represented by the aforementioned general formula (I) or a salt thereof as an active ingredient. According to a preferred embodiment, there is provided the aforementioned plant activator, which is used for control of disease damage of plants. There are also provided an agent for activating an endogenous defense system of a plant, which comprises a compound represented by the aforementioned general formula (I) or a salt thereof as an active ingredient; an agent for inducing disease damage resistance in a plant, which comprises a compound represented by the aforementioned general formula (I) or a salt thereof as an active ingredient; an agent for activating hypersensitive cell death of a plant, which comprises a compound represented by the aforementioned general formula (I) or a salt thereof as an active ingredient; an agent for accelerating phytoalexin production in a plant body, which comprises a compound represented by the aforementioned general formula (I) or a salt thereof as an active ingredient; and an agent for enhancing expression of a disease damage resistance gene in a plant body, which comprises a compound represented by the aforementioned general formula (I) or a salt thereof as an active ingredient. By using a polyamine oxygenase (PAO) inhibitor in combination with a compound represented by the aforementioned general formula (I) or a salt thereof, enhancement of expression of a disease damage resistance gene can be further promoted.

From other aspects, the present invention provides a method for control of disease damage in a plant, which comprises the step of applying a compound represented by the aforementioned general formula (I) or a salt thereof to the plant in an amount effective for the control; a method for activating an endogenous defense system of a plant, which comprises the step of applying a compound represented by the aforementioned general formula (I) or a salt thereof to the plant in an amount effective for the control; a method for inducing disease damage resistance in a plant, which comprises the step of applying a compound represented by the aforementioned general formula (I) or a salt thereof to the plant in an amount effective for the control; a method for activating hypersensitive cell death in a plant after invasion of pathogenic microbes, which comprises the step of applying a compound represented by the aforementioned general formula (I) or a salt thereof to the plant in an amount effective for the control; a method for increasing production amount of a phytoalexin produced in a disease damage resistance response in a plant, which comprises the step of applying a compound represented by the aforementioned general formula (I) or a salt thereof to the plant in an amount effective for the control; a method for enhancing expression of a disease damage resistance gene in a plant, which comprises the step of applying a compound represented by the aforementioned general formula (I) or a salt thereof to the plant in an amount effective for the control; and a method for enhancing expression of a disease damage resistance gene in a plant, which comprises the step of applying a polyamine oxygenase (PAO) inhibitor in combination with a compound represented by the aforementioned general formula (I) or a salt thereof to the plant.

Effect of the Invention

The compounds represented by the aforementioned general formula (I) and salts thereof have an action of activating endogenous defense systems of plants, and can be used as a plant activator, for example, for inducing disease damage resistance in plants and thereby controlling disease damage in the plants. Among the compounds represented by the aforementioned general formula (I), for example, a compound having lauroyl group having one hydroxyl group at the end as $R^1$— has been revealed to be present in plant living bodies, and therefore the plant activator containing a compound represented by the aforementioned general formula (I) or a salt thereof as an active ingredient is useful as a crop protection means that can minimize influences on the ecosystem and reduce stress on the environment.

BRIEF DESCRIPTION OF THE DRAWINGS

FIG. 13, (A) shows the result obtained with HydLau (YIS12OH4N), and (B) shows the result obtained with 1NhydLau (YIS12OH1N).

MODES FOR CARRYING OUT THE INVENTION

Figure 1:
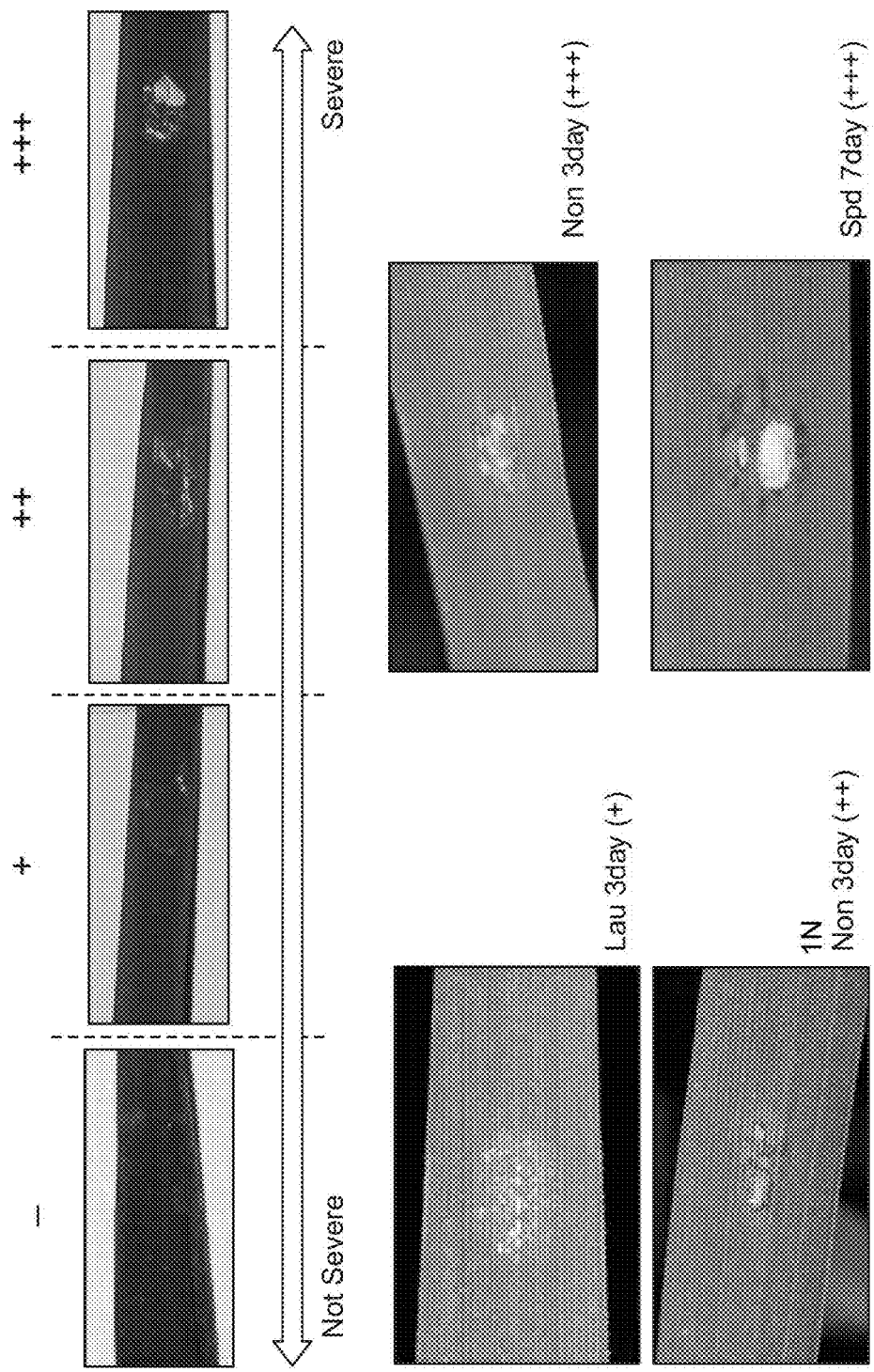
FIG. 1 shows cell death spots observed after applying spermidine derivatives.

In the general formula (I), one of $R^1$ and $R^2$ represents a linear alkanoyl group having 6 to 18 carbon atoms or a linear alkenoyl group having 6 to 18 carbon atoms (the carbon atoms include the carbonyl carbon atom), and the other represents hydrogen atom or a protective group of amino group. $R^3$ represents hydrogen atom or a protective group of amino group. The linear alkanoyl group and the linear alkenoyl group represented by one of $R^1$ and $R^2$ may have 1 to 3 hydroxyl groups, and/or 1 to 3 alkyl groups having 1 to 4 carbon atoms. The alkenoyl group contains double bonds in a number of, for example, about 1 to 3, preferably 2, more preferably 1. Examples of the alkyl group having 1 to 4 carbon atoms, which can exist on the linear alkanoyl group or the linear alkenoyl group, include, for example, methyl group, ethyl group, n-propyl group, isopropyl group, n-butyl group, sec-butyl group, isobutyl group, cyclopropyl group, cyclobutyl group, and the like.

One of $R^1$ and $R^2$ preferably represents a linear alkanoyl group having 8 to 13 carbon atoms, or a linear alkenoyl group having 8 to 13 carbon atoms, and the other represents hydrogen atom or a protective group of amino group. In this case, $R^3$ is preferably hydrogen atom or a protective group of amino group. As the linear alkanoyl group or the linear alkenoyl group, a linear alkanoyl group or linear alkenoyl group having 9 to 12 carbon atoms is preferred. When the linear alkanoyl group or the linear alkenoyl group has hydroxyl group, the number of the hydroxyl group is 1 to 3, and said group can have preferably 1 or 2 hydroxyl groups, more preferably 1 hydroxyl group. As the linear alkanoyl group or the linear alkenoyl group, a linear alkanoyl group or linear alkenoyl group having 9 to 12 carbon atoms and having one hydroxyl group at the end is preferably used. It is more preferred that one of $R^1$ and $R^2$ is a linear alkanoyl group having 9 to 12 carbon atoms, and this linear alkanoyl group may be substituted with one hydroxyl group. It is particularly preferred that $R^1$ or $R^2$ is a linear alkanoyl group having one hydroxyl group at the end, and it is most preferred that $R^1$ or $R^2$ is a linear alkanoyl group having 11 or 12 carbon atoms and having one hydroxyl group at the end.

Type of the protective group of amino group is not particularly limited, and an appropriate protective group can be chosen and used. Those well known in the art as protective group of amino group, for example, a linear or branched alkanoyl group having 2 to 6 carbon atoms such as acetyl group, a linear or branched alkoxycarbonyl group having 2 to 6 carbon atoms such as tert-butoxycarbonyl group and 2,2,2-trichloroethoxycarbonyl group, an aralkyloxycarbonyl group such as benzyloxycarbonyl group, an aralkyl group such as benzyl group and p-methoxybenzyl group, 9-fluorenylmethyloxycarbonyl group, allyloxycarbonyl group, and the like can be preferably used, but the protective group is not limited to these examples. For the protective group of amino group, publications such as Green et al., Protective Groups in Organic Synthesis, 3rd Edition, 1999, John Wiley & Sons, Inc. can be referred to. A particularly preferred protective group is tert-butoxycarbonyl (Boc) group. When two or more of the protective groups of amino group exist in the compound represented by the general formula (I), they may be the same or different, but they are preferably the same protective groups.

When $R^1$ or $R^2$ is a linear alkanoyl group or linear alkenoyl group having hydroxyl group on a carbon atom other than the end carbon atom in the compounds represented by the aforementioned general formula (I), the compounds represented by the aforementioned general formula (I) have one or more asymmetric carbons, and optically active substances or diastereoisomers in pure forms based on one or more asymmetric carbons, any mixtures of isomers (for example, mixture of two or more kinds of diastereoisomers), racemates, and the like fall within the scope of the present invention. When $R^1$ or $R^2$ is a linear alkenoyl group, the compound may exist as E- and Z-geometrical isomers, and these geometrical isomers in pure forms as well as mixtures thereof also fall within the scope of the present invention.

The compounds represented by the aforementioned general formula (I) can form an acid addition salt. Type of the salt is not particularly limited, and examples include salts with mineral acids such as hydrochloric acid and sulfuric acid, salts with organic acids such as p-toluenesulfonic acid, methanesulfonic acid and tartaric acid, and salts with amino acids such as glycine. Furthermore, the compounds represented by the aforementioned formula (I) or a salt thereof may exist as a hydrate or a solvate, and these substances also fall within the scope of the present invention.

The compounds represented by the aforementioned general formula (I) can be prepared by appropriately protecting amino groups of spermidine other than the amino group to be acylated with a protective group of amino group such as tert-butoxycarbonyl group (Boc group), and then acylating the unprotected amino group using an acid halide or the like of carboxylic acid corresponding to the acyl group to be introduced, and by removing the protective groups of amino groups under suitable conditions as required, the compounds not having the protective groups can be obtained in a excellent yield. When an alkanoyl group or alkenoyl group having hydroxyl group is introduced, the hydroxyl group may be appropriately protected beforehand. Type of the protective group of hydroxyl group, introduction conditions of the protective group, and conditions for removing the protective group can be appropriately chosen by referring to publications such as Green et al., Protective Groups in Organic Synthesis, 3rd Edition, 1999, John Wiley & Sons, Inc.

The compounds represented by the aforementioned general formula (I) and salts thereof have an action of activating endogenous defense systems of plants, and can be used to enhance resistance to disease damage of plants. For example, the compounds represented by the aforementioned general formula (I) and salts thereof can activate hypersensitive cell death that induces spontaneous death of cells surrounding an infection lesion after invasion of pathogenic microbes in plants, and can activate the phylaxis system. They can also increase production amount of phytoalexins (for example, phytocassanes A to E, momilactones A and B, etc.) produced in disease damage resistance responses occurring in plants, and can also activate expression of a gene involved in resistance to disease damage in plant bodies. Examples of the disease damage resistance gene include, for example, OsPR1b (Biochem. Biophys. Res. Commun., 278, pp. 290-298, 2000), PBZ1 (Plant Cell Physiol., 37, pp. 9-18, 1996), WRKY45 (Plant Cell, 19, pp. 2064-2076, 2007), OsNPR1 (Mol. Plant-Microbe Interact., 18, pp. 511-520, 2005), and the like. Mol. Geneti. Genomics, 279(4), pp. 415-427, 2008; and Biosci. Biotechnol. Biochem., 65(1), pp. 205-208, 2001 can also be referred to.

On the basis of the aforementioned actions, the compounds represented by the general formula (I) and salts thereof can be used as a plant activator. Type of disease damage of plants is not particularly limited. For example, disease damage induced by infectious diseases caused by fungi, viruses, bacteria, and the like, preferably infectious diseases caused by fungi, can be the object of the control of disease damage, but the object is not limited to disease damage due to these specific diseases.

The plant activator of the present invention can be prepared as a composition for agricultural chemicals, for example, by using pharmaceutical additives well known in this field. Form of the composition for agricultural chemicals is not particularly limited, and any form that can be used in this field may be used. For example, the composition in the form of emulsion, solution, oil, water soluble chemical, wettable powder, floable, dust formulation, fine granule, pellet, aerosol, fumigant, paste agent, or the like can be used. The method for producing the composition for agricultural chemicals is not particularly limited, and methods that can be used by those skilled in the art can be suitably employed. In order to prevent oxidation of the amine moiety in the compounds represented by the general formula (I), it may be preferable to use the active ingredient in the form of a salt such as hydrochloride. A means available as an antioxidant of an active ingredient in a composition for agricultural chemicals may also be suitably employed.

As the active ingredient of the plant activator of the present invention, two or more kinds of the compounds represented by the aforementioned general formula (I) or salts thereof may be used in combination. Depending on a purpose of application, other active ingredients of agricultural chemicals, such as pesticides, fungicides, insecticidal fungicides and herbicides, may be formulated. By applying a polyamine oxygenase (PAO) inhibitor such as guazatine (GAZ) to a plant together with a compound represented by the aforementioned general formula (I) or a salt thereof, enhancement of expression of disease damage resistance gene may further be promoted. Application method and application dose of the plant activator of the present invention can be suitably chosen by those skilled in the art depending on a purpose of application, a form of the activator, application place and the like. For example, a concentration of about 1 to 5 mM can be chosen for rice plant and the like, but the dose is not limited to the aforementioned specific range.

EXAMPLES

Hereafter, the present invention will be still more specifically explained with reference to examples. However, the scope of the present invention is not limited by the following examples.

Example 1

Spermidine (Spd, 4.48 g, 22.7 mmol) was dissolved in dehydrated tetrahydrofuran (THF, 50 ml), and the solution was added with triethylamine (9.75 ml, 68.1 mmol). The mixture was kept at 0° C. and added dropwise with a solution of Boc-ON (13.9 g, 56.5 mmol) dissolved in dehydrated THF (50 ml) with vigorous stirring, and the mixture was stirred overnight at 0° C. After THF was evaporated under reduced pressure, the residue was added with 1M NaOH (50 ml), and the mixture was extracted with dichloromethane (50 ml×3). The organic layers were combined, and washed with brine (50 ml) and $H_2O$ (50 ml×2). After sodium sulfate was added for dehydration, the organic layer was filtered to remove sodium sulfate, and recrystallization was performed in dichloromethane/n-hexane. The produced crystals were washed with n-hexane to obtain $N^1,N^8$-bis-Boc-Spd (6.68 g, 85.4%) as amorphous white crystals.

The resulting $N^1,N^8$-bis-Boc-Spd (83 mg, 0.234 mmol) was dissolved in dichloromethane (10 ml) containing 2% (v/v) of triethylamine, the solution was added with lauroyl chloride (200 µl, excess), and the mixture was stirred at room temperature for 2 hours. After dichloromethane was removed by evaporation under reduced pressure, the residue was added with $H_2O$ (10 ml), the mixture was extracted with ethyl acetate (10 ml×3), and the organic layer was washed with brine (10 ml) and $H_2O$ (10 ml×2). After the organic layer was dehydrated over sodium sulfate, the solvent was evaporated under reduced pressure, and the residue was purified with a silica gel column (ethyl acetate:n-hexane=1:1, v/v). The total amount of the purified compound was added with trifluoroacetic acid (TFA, 2 ml), and the mixture was stirred at room temperature for 30 minutes. Then, the solvent was evaporated under reduced pressure, the residue was added with a small amount of methanol, and the solvent was fully evaporated under reduced pressure again. The residue was washed several times with n-hexane, added with 1M NaOH (5 ml), transferred to a separating funnel, and extracted with dichloromethane (5 ml×4). The organic layer was washed with brine (5 ml) and H$_2$O (10 ml×2), added with sodium sulfate for dehydration, and filtered to obtain N$^4$-lauroyl-Spd (62 mg, 81.0%) as yellow oil.

The other $^4$N-alkanoylspermidines were also synthesized in the same manner as that described above.

Example 2

Diaminobutane (1.2 g, 13 mmol) was dissolved in methanol (10 ml) containing 10% (v/v) of triethylamine, the solution was kept at 0° C. and added dropwise with a solution of Boc$_2$O (1.0 g, 4.6 mmol) dissolved in methanol (2 ml) with vigorous stirring, and the mixture was stirred at 0° C. for 30 minutes and then at room temperature overnight. After the solvent was substantially removed by evaporation under reduced pressure, the residue was dissolved in dichloromethane (20 ml) again, and the solution was washed with 1M NaOH (20 ml) and H$_2$O (20 ml×2). The reaction mixture was added with sodium sulfate for dehydration, and filtered to obtain N-Boc-diaminobutane (589 mg, 69.6%) as yellow oil.

The resulting N-Boc-diaminobutane was dissolved in acetonitrile (20 ml), the solution was added with potassium carbonate (800 mg), and the mixture was added with bromopropylphthalimide (838 mg, 3.13 mmol) with stirring. Then, the reaction mixture was stirred at room temperature for 15 minutes, and then stirred overnight at 45° C. After acetonitrile was evaporated under reduced pressure, the residue was added with H$_2$O (20 ml), and the mixture was extracted with dichloromethane (20 ml×2). The organic layer was washed with brine (10 ml) and H$_2$O (20 ml×2), dehydrated over sodium sulfate, filtered, and concentrated to obtain a crude product as colorless oil. The crude product was purified by silica gel column chromatography (dichloromethane:methanol=9:1, v/v) to obtain N$^8$-Boc-N$^1$-phtal-Spd (695 mg, 59.2%) as colorless oil.

The resulting N$^8$-Boc-N$^1$-phtal-Spd was dissolved in methanol (5 ml) containing 10% (v/v) of triethylamine, the solution was added with Boc$_2$O (0.56 g, 2.52 mmol) with stirring, and the mixture was stirred overnight at room temperature. After the solvent was substantially removed by evaporation under reduced pressure, the residue was added with H$_2$O (10 ml), the mixture was extracted with ethyl acetate (10 ml×2), and the combined organic layer was washed with brine (10 ml) and H$_2$O (10 ml×2). The organic layer was added with sodium sulfate for dehydration, filtered, and purified by silica gel column chromatography (ethyl acetate:n-hexane=1:3, v/v) to obtain N$^4$,N$^8$-bis-Boc-N$^1$-phtal-Spd (332 mg, 81.2%) as colorless oil.

The resulting N$^4$,N$^8$-bis-Boc-N$^1$-phtal-Spd was dissolved in ethanol (1 ml), the solution was added with hydrazine monohydrate (0.2 ml), and the mixture was stirred overnight at room temperature. The reaction mixture was added with H$_2$O (10 ml), the mixture was extracted with dichloromethane (10 ml), and the organic layer was washed with H$_2$O (5 ml×2). The organic layer was added with sodium sulfate for dehydration, and then filtered, and the solvent was evaporated under reduced pressure to obtain N$^4$,N$^8$-bis-Boc-Spd (225 mg, 93.4%) as colorless oil.

N$^4$,N$^8$-bis-Boc-Spd (83 mg, 0.234 mmol) was dissolved in dichloromethane (10 ml) containing 2% (v/v) of triethylamine, the solution was added with lauroyl chloride (200 µl, excess), and the mixture was stirred at room temperature for 2 hours. After dichloromethane was removed by evaporation under reduced pressure, the residue was added with H$_2$O (10 ml), the mixture was extracted with ethyl acetate (10 ml×3), and the organic layer was washed with brine (10 ml) and H$_2$O (10 ml×2). After the organic layer was dehydrated over sodium sulfate, the solvent was evaporated under reduced pressure, and the residue was purified with a silica gel column (ethyl acetate:n-hexane=1:1, v/v). The total amount of the purified compound was added with TFA (2 ml), and the mixture was stirred at room temperature for 30 minutes. Then, the solvent was evaporated under reduced pressure, the residue was added with a small amount of methanol, and then the solvent was fully evaporated under reduced pressure again. The residue was washed several times with n-hexane, and added with 1M NaOH (5 ml), and the mixture was transferred to a separating funnel, and extracted with dichloromethane (5 ml×4). The organic layer was washed with brine (5 ml) and H$_2$O (10 ml×2), then added with sodium sulfate for dehydration, and filtered to obtain $^1$N-lauroyl-Spd (62 mg, 81.0%) as yellow oil.

The other $^1$N-alkanoylspermidines were also synthesized in the same manner as that described above.

TABLE 1

$$H_2N\underset{7}{\hspace{1em}}\underset{}{\hspace{1em}}\underset{5}{\hspace{1em}}\overset{R_1}{\underset{}{N}}\underset{3}{\hspace{1em}}\underset{1}{\hspace{1em}}\overset{H}{\underset{}{N}}R_2$$

positions 8, 6, 4, 2

| Name | R$_1$ | R$_2$ |
|------|-------|-------|
| Hex | —C(O)—(CH$_2$)$_4$CH$_3$ | H |
| Non | —C(O)—(CH$_2$)$_7$CH$_3$ | H |
| Lau | —C(O)—(CH$_2$)$_{10}$CH$_3$ | H |
| Ste | —C(O)—(CH$_2$)$_{16}$CH$_3$ | H |
| Bnz | —C(O)—C$_6$H$_5$ | H |
| Cyn | —C(O)—CH=CH—C$_6$H$_5$ | H |

TABLE 1-continued $H_2N-{}^8CH_2-{}^6CH_2-{}^4N(R_1)-{}^2CH_2-NH-R_2$ (structure with positions 8,7,6,5,4,3,2,1)

| Name | $R_1$ | $R_2$ |
|---|---|---|
| ${}^1$NHex | H | $-C(O)-(CH_2)_4CH_3$ |
| ${}^1$N Non | H | $-C(O)-(CH_2)_7CH_3$ |
| ${}^1$N Lau | H | $-C(O)-(CH_2)_{10}CH_3$ |
| ${}^1$N Ste | H | $-C(O)-(CH_2)_{16}CH_3$ |
| ${}^1$N Bnz | H | $-C(O)-C_6H_5$ |
| ${}^1$N Cyn | H | $-C(O)-CH=CH-C_6H_5$ |

${}^4$N-hexanoylspermidine ${}^1$H NMR (500 MHz CDCl$_3$), δ 0.90 (3H, t, $J_{H,H}$=7.0 Hz, H$_2$-6'), 1.26-1.49 (6H, m, H$_2$-3'~5'), 1.54-1.73 (6H, m, H$_2$-2,6,7), 2.29 (2H, m, H$_2$-2'), 2.64-2.77 (4H, m, H$_2$-1,8), 3.21-3.46 (4H, m, H$_2$-3,5)

${}^4$N-nonanoylspermidine ${}^1$H NMR (500 MHz CDCl$_3$), δ 0.88 (3H, t, $J_{H,H}$=6.5 Hz, H$_2$-9'), 1.22-1.36 (10H, m, H$_2$-(4'~8'), 1.45 (2H, m, H$_2$-3'), 1.53-1.73 (6H, m, H$_2$-2,6,7), 2.29 (2H, m, H$_2$-2'), 2.64-2.76 (4H, m, H$_2$-1,8), 3.21-3.44 (4H, m, H$_2$-3,5)

${}^4$N-lauroylspermidine ${}^1$H NMR (500 MHz CDCl$_3$), δ 0.88 (3H, t, $J_{H,H}$=6.8 Hz, H$_2$-12'), 1.26-1.30 (16H, m, H$_2$-4'-11'), 1.45 (2H, m, H$_2$-3'), 1.50-1.73 (6H, m, H$_2$-2,6,7), 2.29 (2H, m, H$_2$-2'), 2.64-2.76 (4H, m, H$_2$-1,8), 3.24-2.42 (4H, m, H$_2$-3,5)

${}^4$N-stearoylspermidine ${}^1$H NMR (500 MHz CDCl$_3$), δ 0.88 (3H, t, $J_{H,H}$=7.0 Hz, H$_2$-18'), 1.20-1.35 (28H, m, H$_2$-4'~17'), 1.46 (2H, m, H$_2$-3'), 1.54-1.74 (6H, m, H$_2$-2,6,7), 2.29 (2H, m, H$_2$-2'), 2.66-2.76 (4H, m, H$_2$-1,8), 3.23-3.45 (4H, m, H$_2$-3,5)

${}^4$N-benzoylspermidine ${}^1$H NMR (500 MHz CDCl$_3$), δ 1.45-1.86 (6H, m, H$_2$-2,6,7), 2.48-2.73 (4H, m, H$_2$-1,8), 3.18-3.63 (4H, m, H$_2$-3,5), 7.32-7.44 (5H, m, Ph)

${}^4$N-cinnamoylspermidine ${}^1$H NMR (500 MHz CDCl$_3$), δ 1.47-1.79 (6H, m, H$_2$-2,6,7), 2.71-2.80 (4H, m, H$_2$-1,8), 3.41-3.57 (4H, m, H$_2$-3,5), 6.84-7.00 (1H, dd, $J_{H,H}$=68.1 Hz, 15.6 Hz, CHPh), 7.21-7.52 (5H, m, Ph), 7.68-7.72 (1H, dd, $J_{H,H}$=15.3 Hz, 5.5 Hz, CHCO)

${}^1$N-hexanoylspermidine ${}^1$H NMR (500 MHz CDCl$_3$), δ 0.89 (3H, t, $J_{H,H}$=6.8 Hz, H$_2$-6'), 1.31 (4H, m, H$_2$-4',5'), 1.48-1.70 (8H, m, H$_2$-2,6,7,3'), 2.15 (2H, t, $J_{H,H}$=7.6 Hz, H$_2$-2'), 2.62 (2H, t, $J_{H,H}$=6.8 Hz, H$_2$-8), 2.72 (4H, m, H$_2$-3,5), 3.34 (2H, dt, $J_{H,H}$=6.1 Hz, 6.1 Hz, H$_2$-1), 6.88 (1H, s, —NHCO—)

${}^1$N-nonanoylspermidine ${}^1$H NMR (500 MHz CDCl$_3$), δ 0.88 (3H, t, $J_{H,H}$=6.9 Hz, H$_2$-9'), 1.21-1.34 (10H, m, H$_2$-4'-8'), 1.44-1.69 (8H, m, H$_2$-2,6,7,3'), 2.14 (2H, t, $J_{H,H}$=7.6 Hz, H$_2$-2'), 2.61 (2H, t, $J_{H,H}$=6.9 Hz, H$_2$-8), 2.71 (4H, m, H$_2$-3,5), 3.34 (2H, dt, $J_{H,H}$=6.1 Hz, 6.1 Hz, H$_2$-1), 6.69 (1H, s, —NHCO)

${}^1$N-lauroylspermidine ${}^1$H NMR (500 MHz CDCl$_3$), δ 0.88 (3H, t, $J_{H,H}$=6.9 Hz, H$_2$-12'), 1.22-1.33 (16H, m, H$_2$-4'-11'), 1.46-1.70 (8H, m, H$_2$-2,6,7,3'), 2.15 (2H, t, $J_{H,H}$=7.6 Hz, H$_2$-2'), 2.62 (2H, t, $J_{H,H}$=6.9 Hz, H$_2$-8), 2.72 (4H, m, H$_2$-3,5), 3.35 (2H, dt, $J_{H,H}$=6.1 Hz, 6.1 Hz, H$_2$-1), 6.70 (1H, s, —NHCO)

${}^1$N-stearoylspermidine ${}^1$H NMR (500 MHz CDCl$_3$), δ 0.88 (3H, t, $J_{H,H}$=7.0 Hz, H$_2$-18'), 1.20-1.32 (28H, m, H$_2$-4'-17'), 1.46-1.69 (8H, m, H$_2$-2,6,7,3'), 2.14 (2H, t, $J_{H,H}$=7.6 Hz, H$_2$-2'), 2.61 (2H, t, $J_{H,H}$=6.9 Hz, H$_2$-8), 2.72 (4H, m, H$_2$-3,5), 3.34 (2H, dt, $J_{H,H}$=6.0 Hz, 6.0 Hz, H$_2$-1), 6.68 (1H, s, —NHCO)

${}^1$N-benzoylspermidine ${}^1$H NMR (500 MHz CDCl$_3$), 1.43-1.58 (4H, m, H$_2$-6,7), 1.78 (2H, qi, H$_2$-2), 2.65 (2H, t, $J_{H,H}$=7.0 Hz, H$_2$-8), 2.69 (2H, t, $J_{H,H}$=6.9 Hz, H$_2$-5), 2.83 (2H, t, $J_{H,H}$=5.8 Hz, H$_2$-3), 3.58 (2H, m, $J_{H,H}$=5.7 Hz, 5.7 Hz, H$_2$-1), 7.41 (2H, m, H$_{ph}$-3,5), 7.48 (1H, m, H$_{ph}$-4), 7.80 (2H, m, H$_{ph}$-2,6), 8.20 (1H, s, —NHCO)

${}^1$N-cinnamoylspermidine ${}^1$H NMR (500 MHz CDCl$_3$), δ 1.48-1.59 (4H, m, H$_2$-6,7), 1.74 (2H, qi, $J_{H,H}$=6.3 Hz, H$_2$-6), 2.64 (2H, t, $J_{H,H}$=7.0 Hz, H$_2$-5), 2.72 (2H, t, $J_{H,H}$=6.5 Hz, H$_2$-3), 2.77 (2H, dt, $J_{H,H}$=6.0 Hz, 6.0 Hz, H$_2$-3), 3.48 (2H, m, H$_2$-1), 6.38 (1H, dd, $J_{H,H}$=15.5 Hz, CHPh), 7.22-7.51 (5H, m, Ph), 7.59 (1H, dd, $J_{H,H}$=15.5 Hz, CHCO)

Example 3

Compounds in which lauroyl group introduced with one hydroxyl group at the end was bound to the 1-position or the 4-position were synthesized as follows.

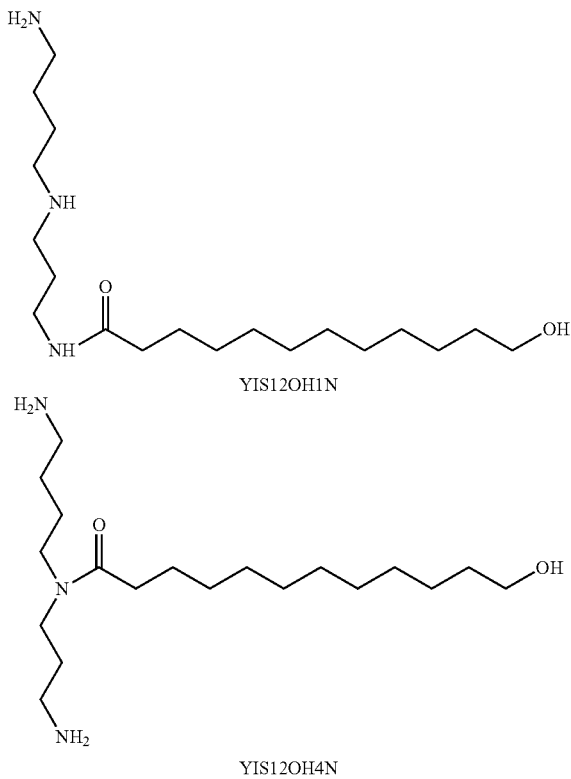

[Formula 1]

YIS12OH1N

YIS12OH4N

12-Hydroroxylauric acid (225 mg, 1.04 mmol) was added with dichloromethane (10 ml), and the mixture was added with EDCI (200 mg, 1.04 mmol) and DMAP (127 mg, 1.04 mmol) under a nitrogen gas atmosphere, and the mixture was stirred until all the substances were dissolved. The solution was added with $^1$N,$^8$N-diBoc-spermidine (300 mg, 0.870 mmol) dissolved in dichloromethane (5 ml), and the mixture was stirred at room temperature for 3 days under a nitrogen gas atmosphere.

After completion of the stirring, the reaction mixture was added with aqueous citric acid (10%, w/w, 10 ml), the mixture was stirred for 5 minutes to terminate the reaction, and extracted with dichloromethane (10 ml×3). The organic layer was dehydrated over sodium sulfate, and the solvent was evaporated under reduced pressure to obtain a crude product (0.62 g) as colorless oil. The crude product was purified by silica gel column chromatography (ethyl acetate:n-hexane=4:1) to obtain 1N,$^8$N-diBoc-$^4$N-(12-hydroxylauroyl)-spermidine (155 mg, 32.8%) as colorless oil. $^1$H NMR (500 MHz, CDCl$_3$), δ 1.28 (16H, s, H$_2$-4'-11'), 1.44 (20H, m, 2× Boc, H$_2$-3'), 1.56-1.69 (6H, m, H$_{2-2, 6, 7}$), 2.34 (2H, t, J$_{H,H}$=7.5 Hz, H$_2$-2'), 3.07-3.40 (9H, m, H$_2$-1, 3, 5, 8, —OH), 3.62 (2H, t, J$_{H,H}$=6.5 Hz, H$_2$-12')

The above product was stirred in trifluoroacetic acid/dichloromethane (20% v/v, 10 ml) for 1 hour, trifluoroacetic acid was evaporated under reduced pressure by azeotropy with methanol, and the residue was added with 1 M NaOH (5 ml). The mixture was transferred to a separating funnel, and extracted with dichloromethane (5 ml×4), and the organic layer was washed with distilled water (5 ml), and dehydrated over sodium sulfate. Then, the solvent was evaporated under reduced pressure to obtain $^4$N-(12-hydroroxylauroyl)-spermidine (73 mg, 24.5%) as amorphous white crystals.

12-Hydroroxylauric acid (300 mg, 1.39 mmol) was added with dichloromethane (15 ml), the mixture was added with EDCI (275 mg, 1.39 mmol) and DMAP (170 mg, 1.39 mmol) under a nitrogen gas atmosphere, and the mixture was stirred until all the substances were dissolved. The solution was added with $^4$N,$^8$N-diBoc-spermidine (400 mg, 1.16 mmol) dissolved in dichloromethane (5 ml), and the mixture was stirred at room temperature for 3 days under a nitrogen gas atmosphere.

After completion of the stirring, the reaction mixture was added with aqueous citric acid (10%, w/w, 10 ml), and the mixture was stirred for 5 minutes to terminate the reaction, and extracted with dichloromethane (10 ml×3). The organic layer was dehydrated over sodium sulfate, and the solvent was evaporated under reduced pressure to obtain a crude product (0.68 g) as colorless oil. The crude product was purified by silica gel column chromatography (ethyl acetate:n-hexane=4:1) to obtain $^4$N,$^8$N-diBoc-$^1$N-(12-hydroroxylauroyl)-spermidine (311 mg, 49.3%) as colorless oil.

1H NMR (500 MHz, CDCl$_3$), δ 1.27 (16H, s, H$_2$-4'-11'), 1.44 (20H, m, 2× Boc, H$_2$-3'), 1.51-1.64 (6H, m, H$_2$-2,6,7), 2.18 (2H, t, J$_{H,H}$=7.8 Hz, H$_2$-2'), 3.13-3.28 (9H, m, H$_2$-1, 3, 5, 8, —OH), 3.63 (2H, m, H$_2$-12')

The above product was stirred in trifluoroacetic acid/CH$_2$Cl$_2$ (20% v/v, 10 ml) for 1 hour, trifluoroacetic acid was evaporated under reduced pressure by azeotropy with methanol, then the residue was added with 1M NaOH (5 ml), and the mixture was transferred to a separating funnel, and extracted with dichloromethane (5 ml×4). The organic layer was washed with distilled water (5 ml), and dehydrated over sodium sulfate, and then the solvent was evaporated under reduced pressure to obtain 1-N-(12-hydroroxylauroyl)-spermidine (160 mg, 40.2%) as amorphous white crystals.

YIS12OH1N (compound formed by binding —CO—(CH$_2$)$_{10}$CH$_2$—OH to the amino group at the 1-position of spermidine)

$^1$H NMR (500 MHz, CDCl$_3$), δ 1.28 (16H, m, H$_2$-4'-11'), 1.44-1.67 (9H, m, H$_2$-2,6,7,3', —OH), 2.30 (2H, m, H$_2$-2'), 2.64-2.76 (4H, m, H$_2$-1,8), 3.00-3.47 (4H, m, H$_2$-3,5), 3.62 (2H, t, J$_{H,H}$=6.5 Hz, H$_2$-1')

YIS12OH4N (compound formed by binding —CO—(CH$_2$)$_{10}$CH$_2$—OH to the amino group at the 4-position of spermidine)

$^1$H NMR (500 MHz CDCl$_3$) δ 1.28 (16H, m, H$_2$-4'-11'), 1.50-1.67 (9H, m, H$_2$-2,6,7,3', —OH), 2.14 (2H, t, J$_{H,H}$=7.5 Hz, H$_2$-2'), 2.61 (2H, t, J$_{H,H}$=6.8 Hz, H$_2$-8), 2.71 (4H, m, H$_2$-3,5), 3.35 (2H, dt, J$_{H,H}$=6.0 Hz, 6.0 Hz, H$_2$-1), 3.63 (2H, t, J$_{H,H}$=6.5 Hz, H$_2$-12), 6.73 (1H, s, —NHCO)

Example 4

Figure 2:
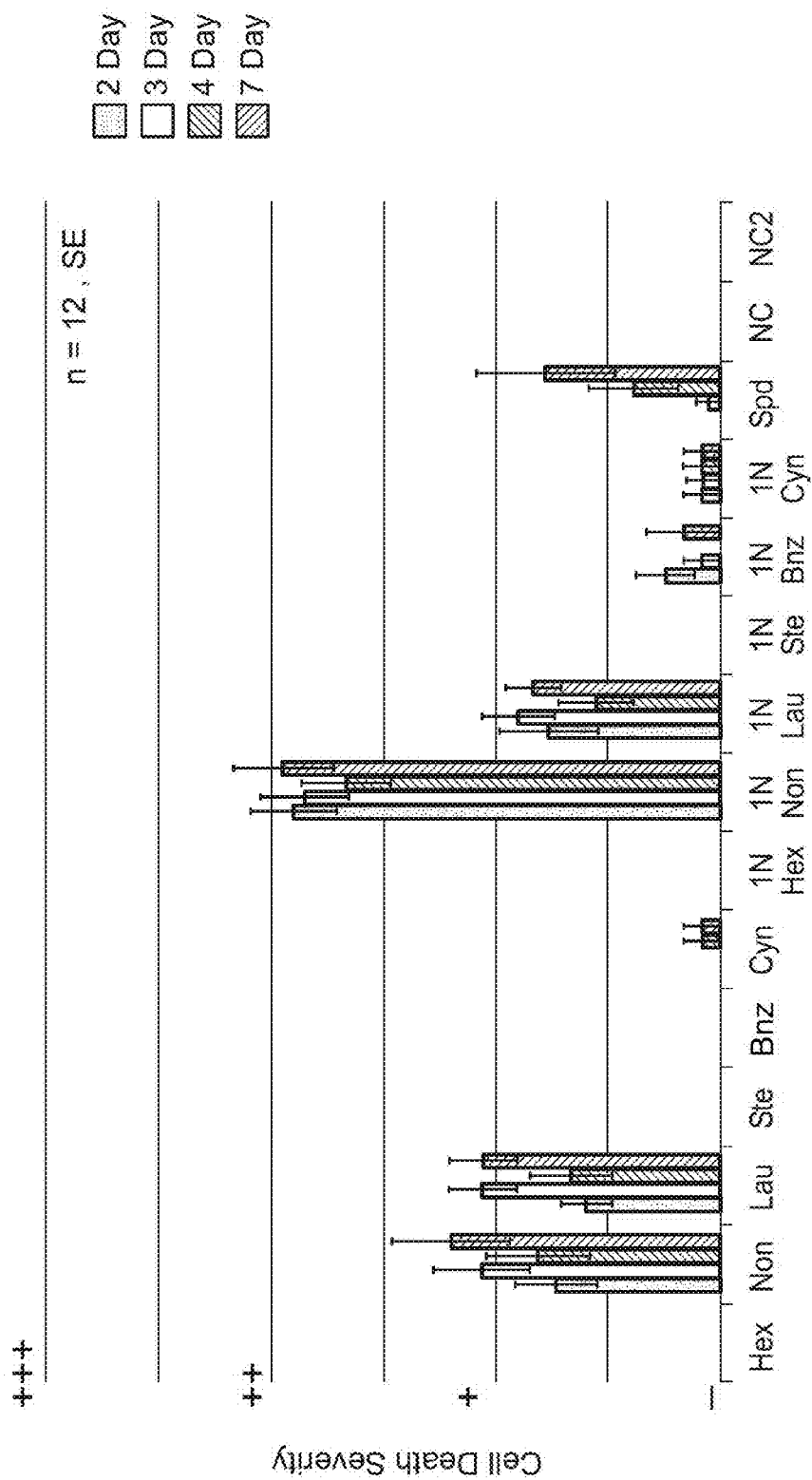
FIG. 2 shows severity of cell death induced by applying spermidine derivatives.

It is known that spermidine treatment of leaf blades forms HR (Hypersensitive Response) like cell death spots in various plant species (Plant Physiol., 132(4), pp. 1973-1981, 2009). 1 mM Aqueous solutions (added with Tween 20 at a final concentration of 0.1%) of the spermidine derivatives obtained in Example 1 were each dropped in a volume of 5 μl on a leaf blade of rice plant (variety name: Nipponbare) about one month after seeding, and air-dried as it was, and severity of the cell death observed thereafter was visually evaluated on the basis of severity and ratio to dropped area of cell death (FIGS. 1 and 2). As a result, formation of fine cell death spots different from those formed with spermidine (Spd) itself were observed for Non, Lau, $^1$N Non, $^1$N Lau, and the like. Moreover, whereas the cell death induced by Spd was observed only in a part of the treated leaves, these spermidine derivatives formed cell death spots on more treated leaves at an earlier stage compared with spermidine.

Example 5

Figure 3:
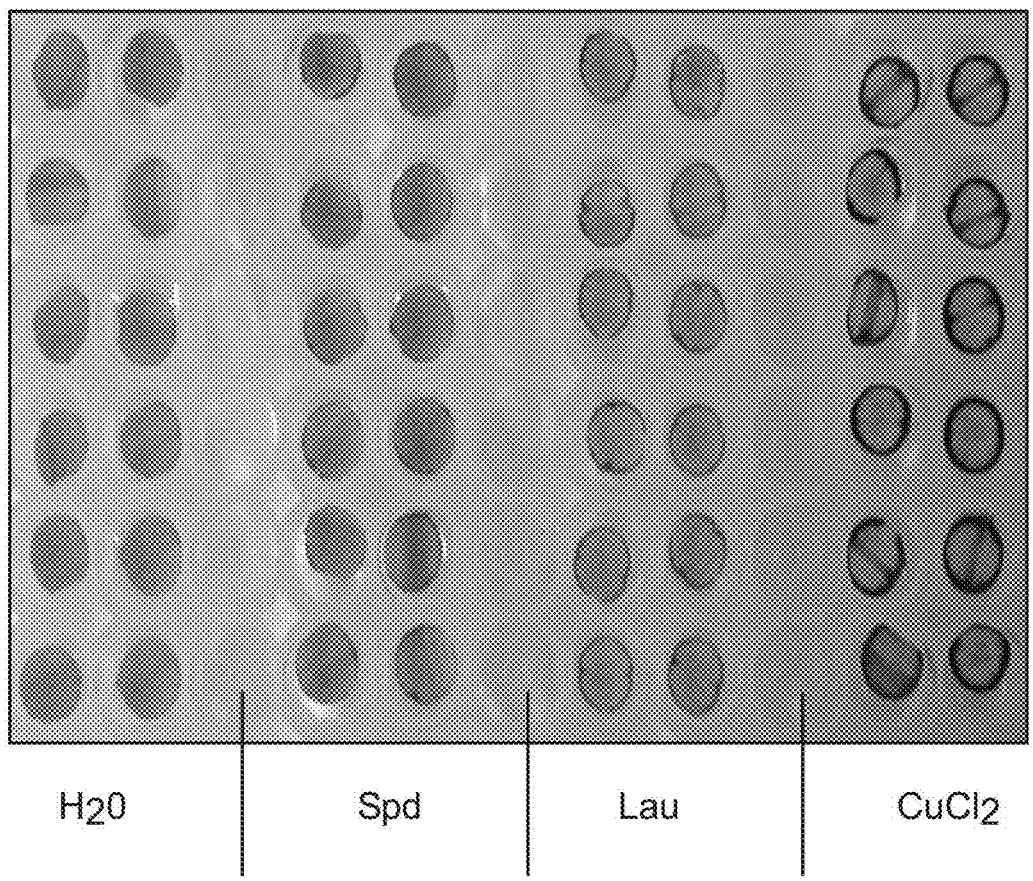
FIG. 3 shows leaf disks treated in an aqueous solution of spermidine or a spermidine derivative (Lau) for 72 hours.
Figure 4:
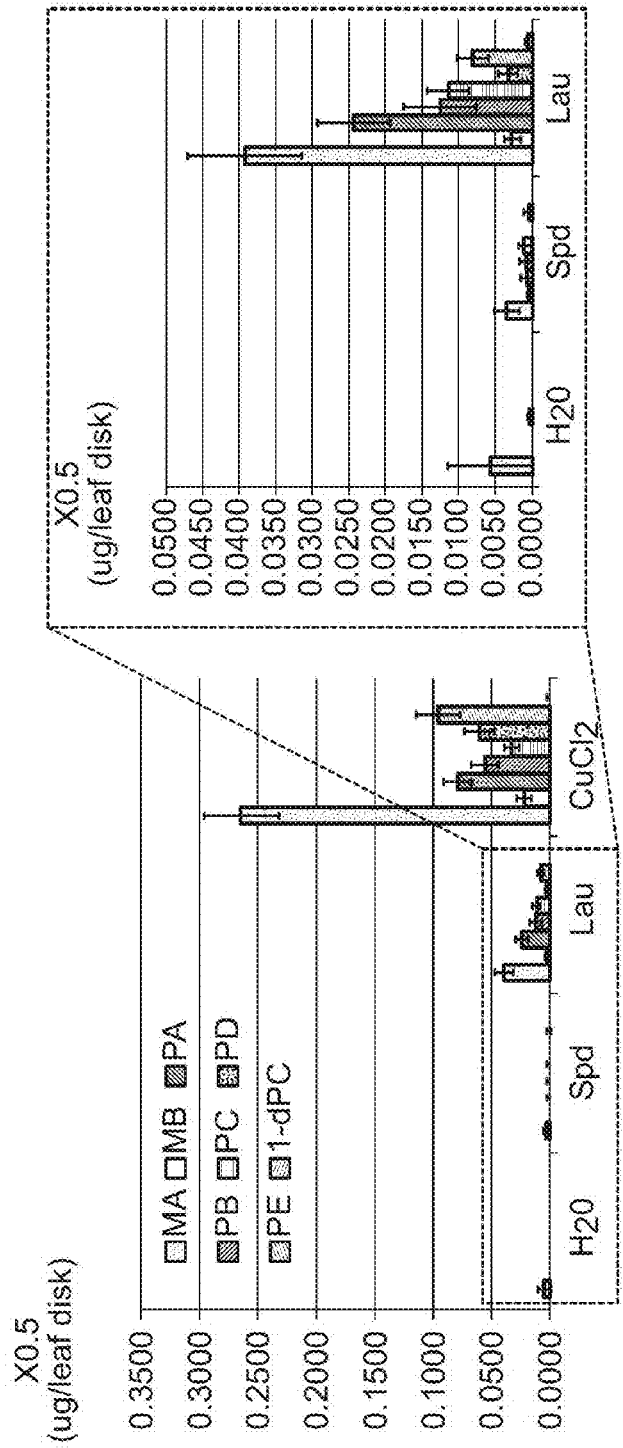
FIG. 4 shows phytoalexin production amounts observed after treatment in an aqueous solution of spermidine or a spermidine derivative (Lau) for 72 hours. The graph on the right is an enlarged graph of a part of the graph on the left.

Phytoalexins are antimicrobial substances produced in disease damage resistance responses in plants, and phytocassanes A to E (PA to PE), momilactones A and B (MA and MB), and the like are known. Leaf disks were cut out from rice plant leaf blades, a 0.5 mM aqueous solution of spermidine or Lau, for which potent cell death induction effect was observed in Example 2, was prepared, the leaf disks were immersed in the aqueous solution, and phytoalexin production amount was measured after 72 hours. As a result, browning of leaf disks, which is a reaction specific to copper chloride known as a phytoalexin production-inducing substance, and evident phytoalexin accumulation were observed with the Lau treatment, although they were not so severe compared with those observed with copper chloride (FIGS. 3 and 4).

Example 6

Figure 5:
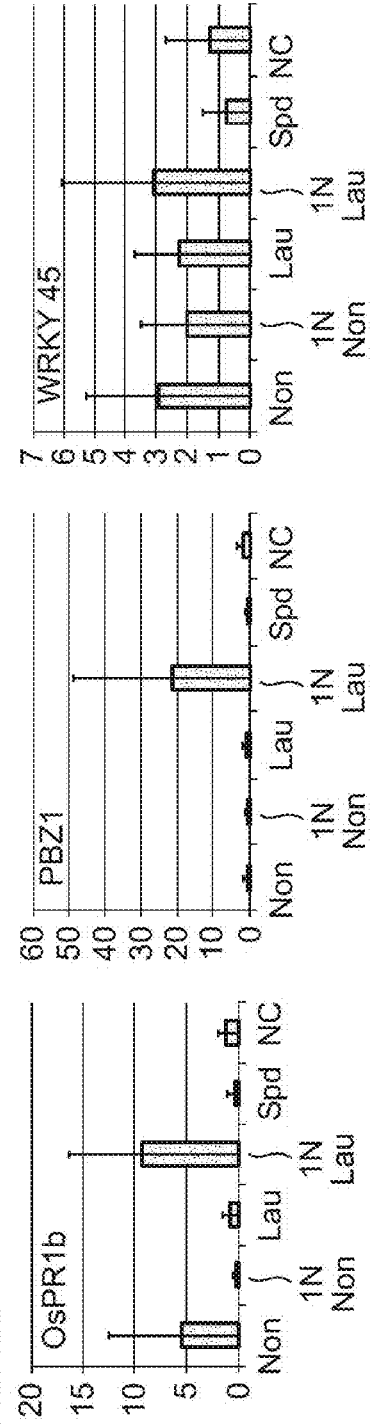
FIG. 5 shows expression amounts of resistance related genes in rice plant leaf blades treated with spermidine derivatives.

1 mM Aqueous solutions of the spermidine derivatives were prepared, and added with Tween 20 at a final concentration of 0.01%. Each solution was sprayed on leaf blades of the rice plant cultivated for one week by hydroponics, and after 24 hours, RNAs were extracted. Expression of OsPR1b, PBZ1 and WRKY45, which are rice plant disease damage resistance marker genes, in each sample was measured by using real-time PCR. As a result, there was observed a tendency that the spermidine derivatives induced expression of the resistance marker genes (FIG. 5).

Figure 6:
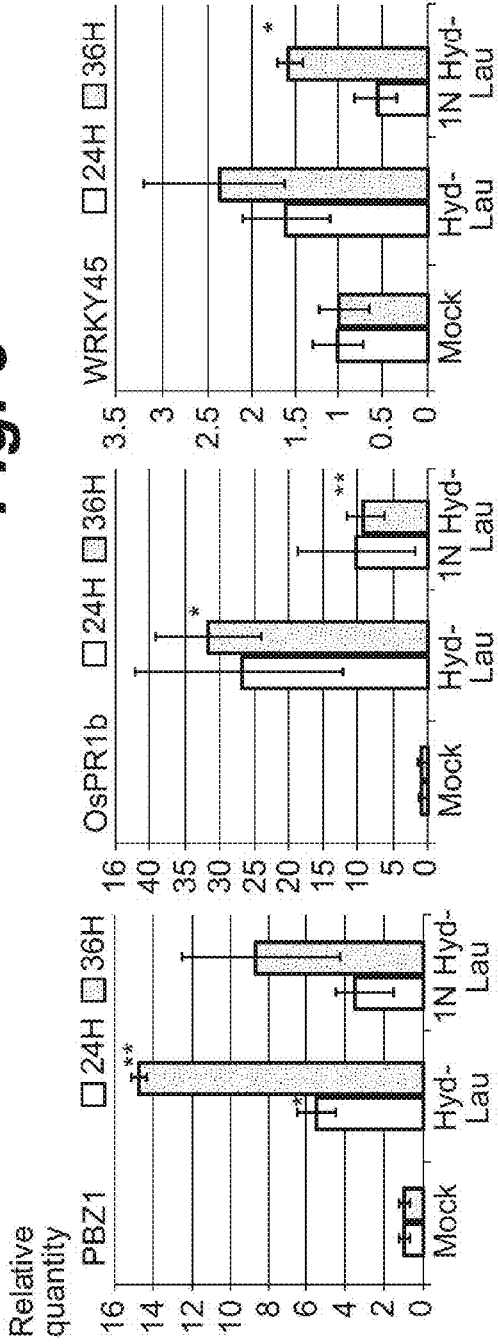
FIG. 6 shows expression amounts of resistance related genes in rice plant leaf blades treated with YIS12OH1N (1NHydLau) or YIS12OH4N (HydLau). Mock denotes the results obtained with a treatment using a solution not containing a test compound.

1 mM Aqueous solutions of YIS12OH1N (1NHydLau) and YIS12OH4N (HydLau) were prepared, and added with Tween 20 at a final concentration of 0.01%. Each solution was sprayed on leaf blades of the rice plant cultivated for one week by hydroponics, and after 24 hours, RNAs were extracted. Expression of OsPR1b, PBZ1 and WRKY45, which are rice plant disease damage resistance marker genes, in each sample was measured by using real-time PCR. As a result, there was observed a tendency that these spermidine derivatives induced expression of the resistance marker genes (FIG. 6).

Example 7

Figure 7:
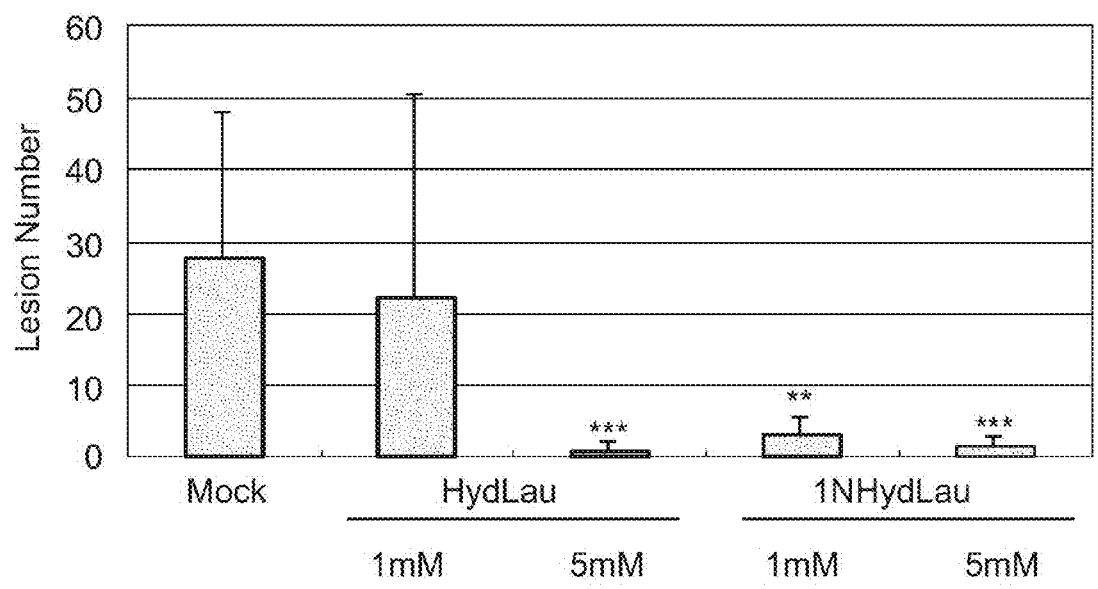
FIG. 7 shows results of measurement of lesion number in rice plants at the five-leaf stage treated with spraying of YIS12OH1N (1NHydLau) or YIS12OH4N (HydLau), then inoculated and infected with a rice blast fungus, which measurement was performed 6 days after the inoculation. Mock denotes the results obtained with spraying of a solution not containing a test compound. In the graph, significant differences at 1% and 0.1% levels are indicated with  and *, respectively.
Figure 8:
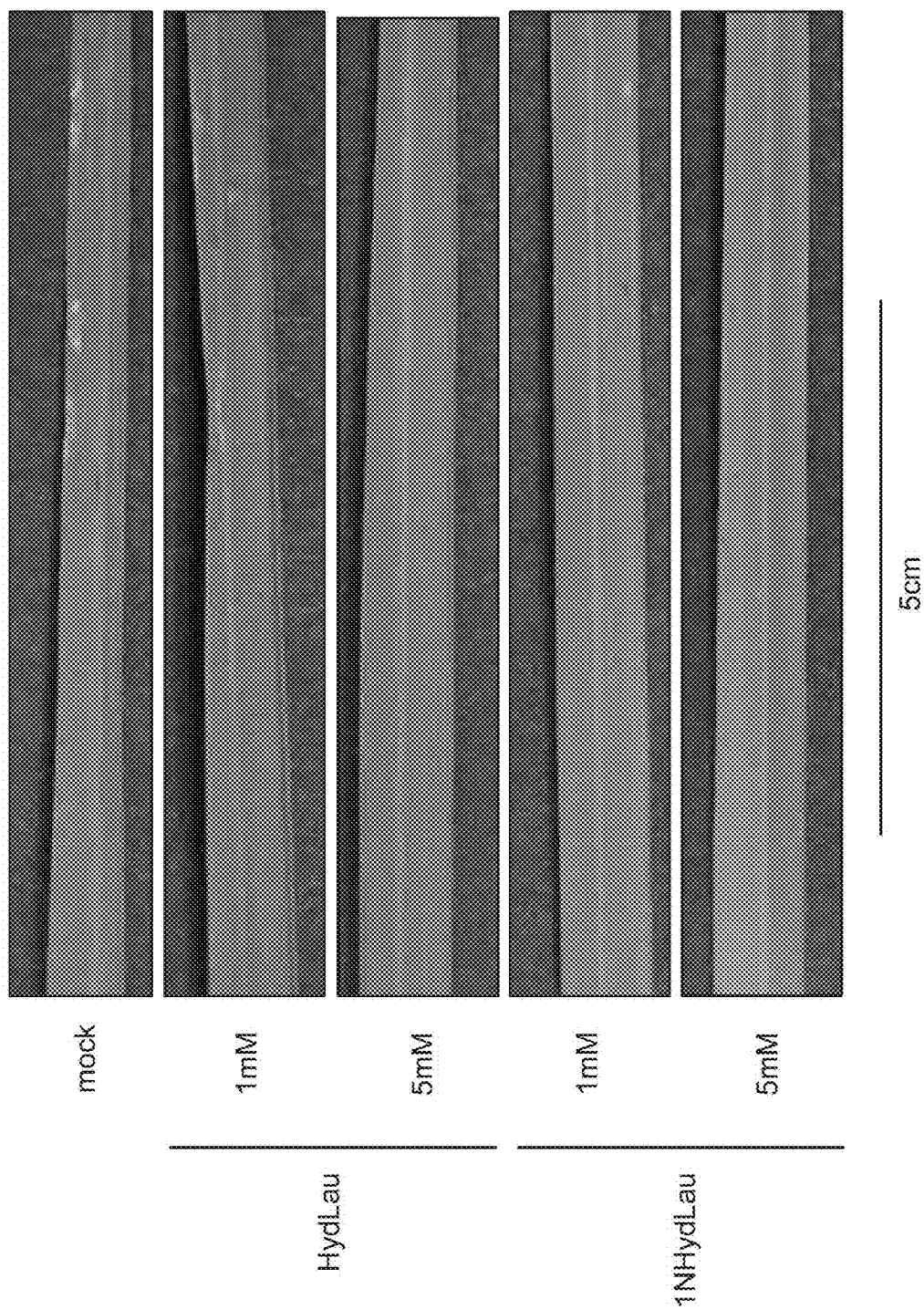
FIG. 8 shows results of observation of rice plants at the five-leaf stage treated with spraying of YIS12OH1N or YIS12OH4N, then inoculated and infected with a rice blast fungus, which observation was performed 6 days after the inoculation.
Figure 9:
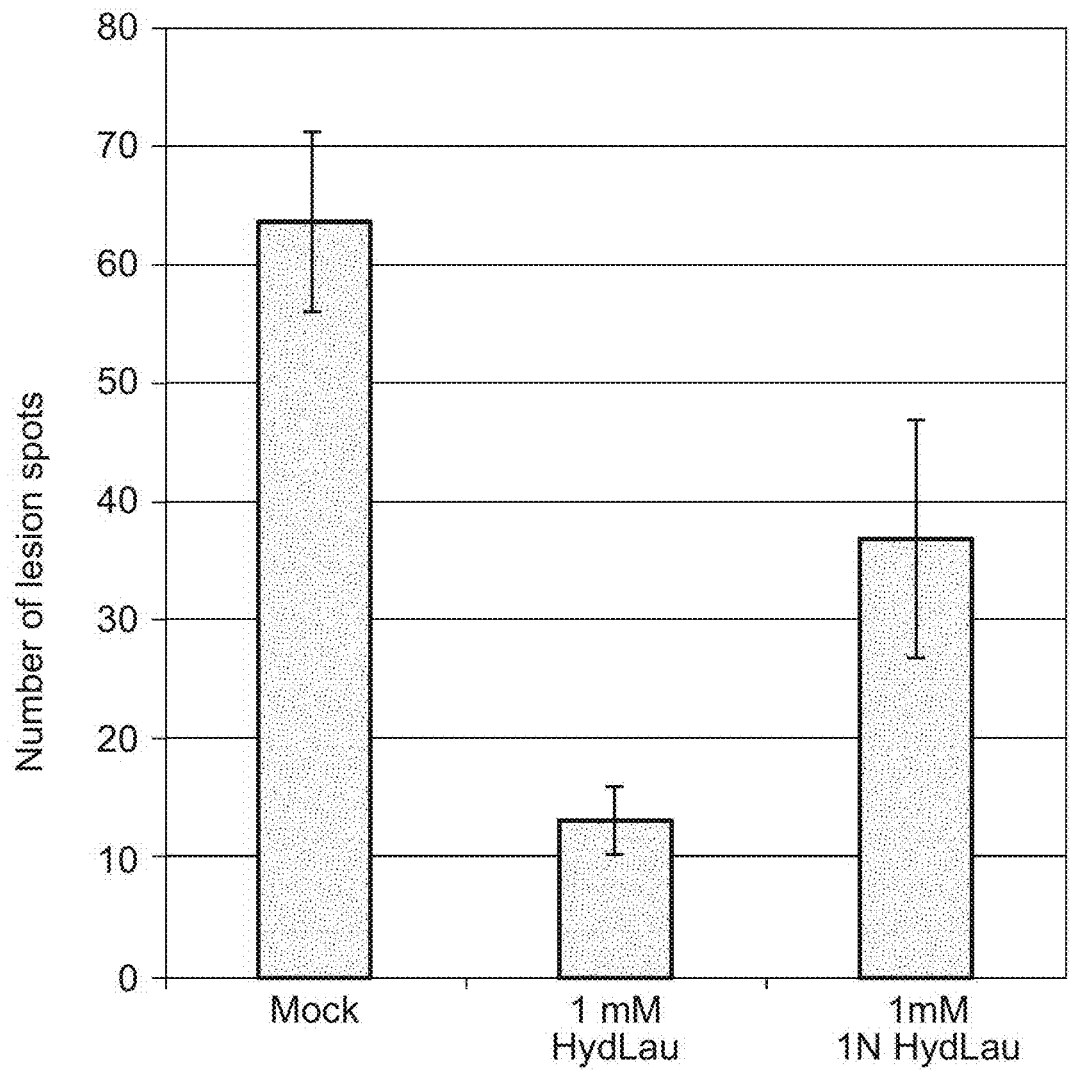
FIG. 9 shows results of measurement of lesion number in rice plants at the five-leaf stage treated with spraying of YIS12OH1N (1NHydLau) or YIS12OH4N (HydLau), then inoculated and infected with a rice blast fungus, which measurement was performed 6 days after the inoculation. Mock denotes the results obtained with spraying of a solution not containing a test compound.

The rice plants at the five-leaf stage were treated with spraying of YIS12OH1N (1NHydLau) or YIS12OH4N (HydLau) at a concentration of 1 mM or 5 mM, inoculated and infected with a rice blast fungus (Kyu89-246, MAFF101506, race 003.0, $3.4 \times 10^5$ spores/ml) on the next day. The results of measurement of the number of lesions performed 6 days after the inoculation are shown in FIGS. 7 and 8. The rice plant treated with the spraying without any test compound (Mock) was infected by rice blast, and as a result many lesions appeared in the same, whilst the rice plant treated with YIS12OH1N or YIS12OH4N at a concentration of 5 mM showed resistance to rice blast. YIS12OH1N provided the resistance even with the treatment at 1 mM. When only the test compounds were sprayed (5 mM), cell death spots were not observed. In the same manner, the rice plants at the five-leaf stage were treated with spraying of YIS12OH1N (1NHydLau) or YIS12OH4N (HydLau) at a concentration of 1 mM, inoculated and infected with the rice blast fungus (Kyu89.246, MAFF 101506, race 003.0, $3.4 \times 10^5$ spores/ml) on the next day. The results of measurement of the number of lesions performed 6 days after the inoculation are shown in FIG. 9.

Example 8

Figure 10:
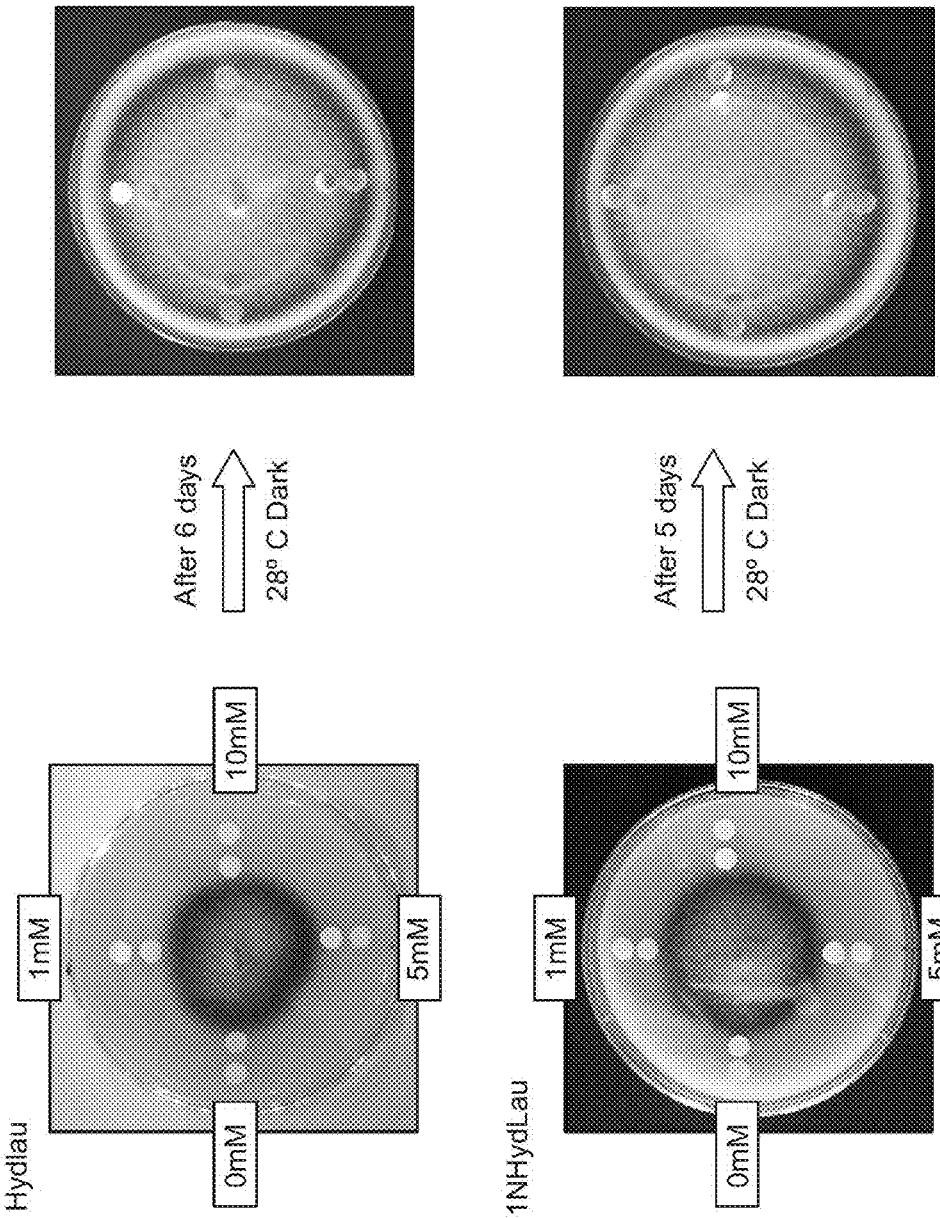
FIG. 10 shows results of examination of antifungal action of YIS12OH1N or YIS12OH4N against the rice blast fungus determined on the basis of the presence or absence of formation of inhibition ring.

Filter paper disks having a diameter of 6 mm were each infiltrated with 20 of an aqueous solution of YIS12OH1N (1NHydLau) or YIS12OH4N (HydLau) (1 mM, 5 mM or 10 mM), and air-dried, and formation of inhibition rings against the rice blast fungus (Kyu89-246, MAFF101506, race 003.0) was evaluated by using these filter paper disks. Formation of inhibition ring was not observed after culture at 28° C. for 5 to 6 days under light shielding (FIG. 10), and accordingly, it was revealed that these compounds per se did not have antifungal activity against the rice blast fungus even at the 10 mM concentration.

Example 9

Figure 11:
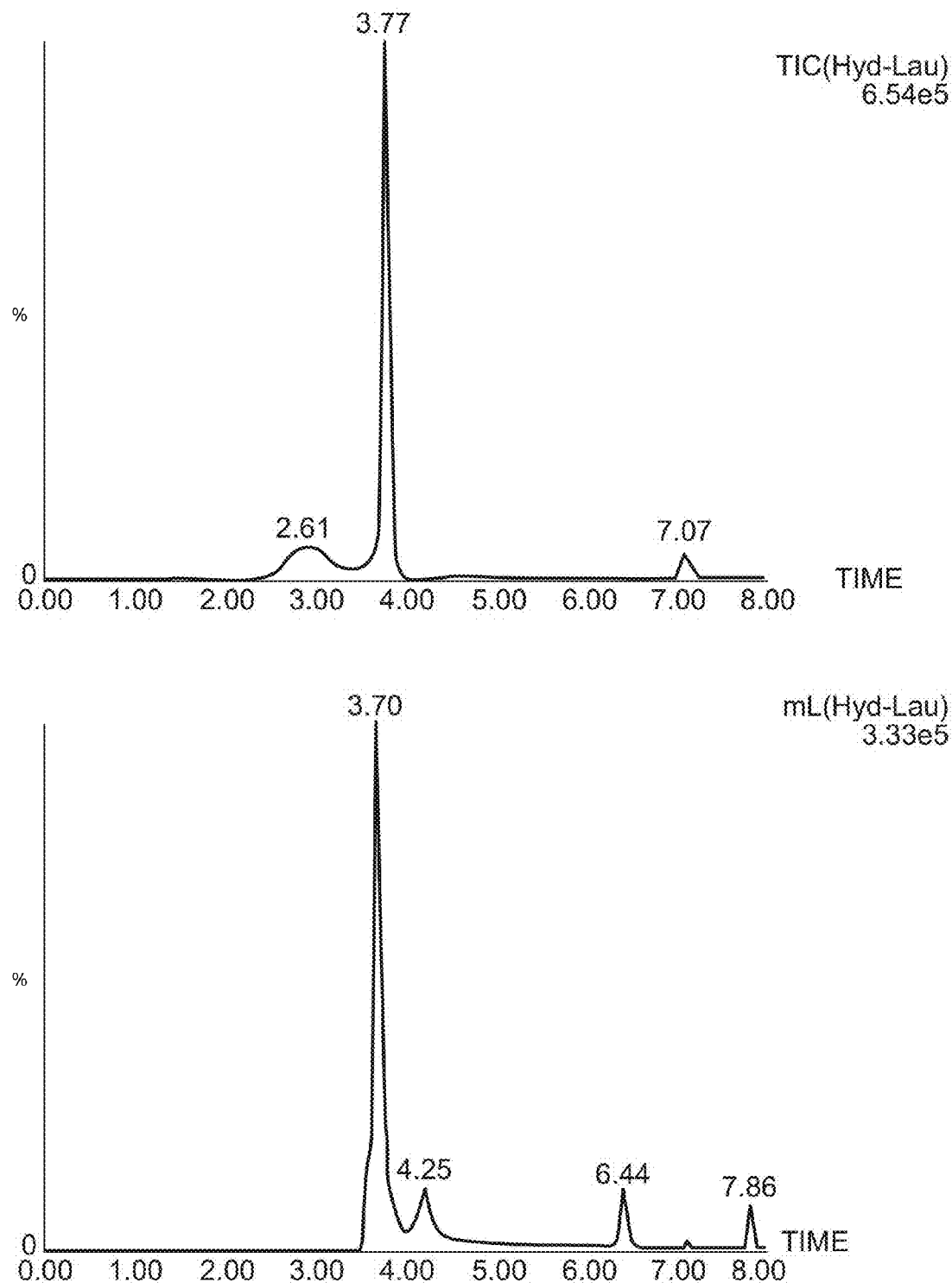
FIG. 11 shows results of identification of natural YIS12OH4N existing in a rice plant overexpressing OsAT1, carried out by using a synthesized sample of the same.

Leaf blades of OsAT1-overexpressing rice plant subjected to frozen crashing using $LN_2$ were extracted with methanol, and then the extract was subjected to solvent fractionation with 1 M NaOH—$CH_2Cl_2$, and substances were collected from the organic layer with 1M HCl, and purified with Oasis (registered trademark) column to prepare a sample. Natural YIS12OH4N existing in the rice plant was identified by LC/MS using a synthesized sample of YIS12OH4N. The results are shown in FIG. 11. It was revealed that YIS12OH4N existed in the OsAT1-overexpressing rice plant. The measurement conditions of LC/MS were as follows.

Waters Acquity UPLC
Column: ACQUITY C18BEH (1.7 μm, 2.1×50 mm) column
Flow rate: 0.2 mL/min
Mobile phase A: 0.1% aqueous formic acid, B: 0.1% formic acid in methanol
Gradient Conditions

| Min | flow | A | B |
| --- | --- | --- | --- |
| 0 | 0.2 | 70 | 30 |
| 1 | 0.2 | 70 | 30 |
| 10 | 0.2 | 0 | 100 |

Waters Xevo (registered trademark) TQ MS
Capillary voltage: 3.0 kV
Cone voltage: 34 V
Source temperature: 150° C.
Desolvation temperature: 400° C.
Cone gas flow rate: 50 L/Hr
Desolvation gas flow rate: 800 L/Hr
Detection mode: MRM mode (positive)
Collision voltage: 22/16 V (Ch1/Ch2)
Channel condition: 344.46>256.30/344.46>273.34 (Ch1/Ch2)
Data analysis: MassLynx (registered trademark)

Example 8

Figure 12:
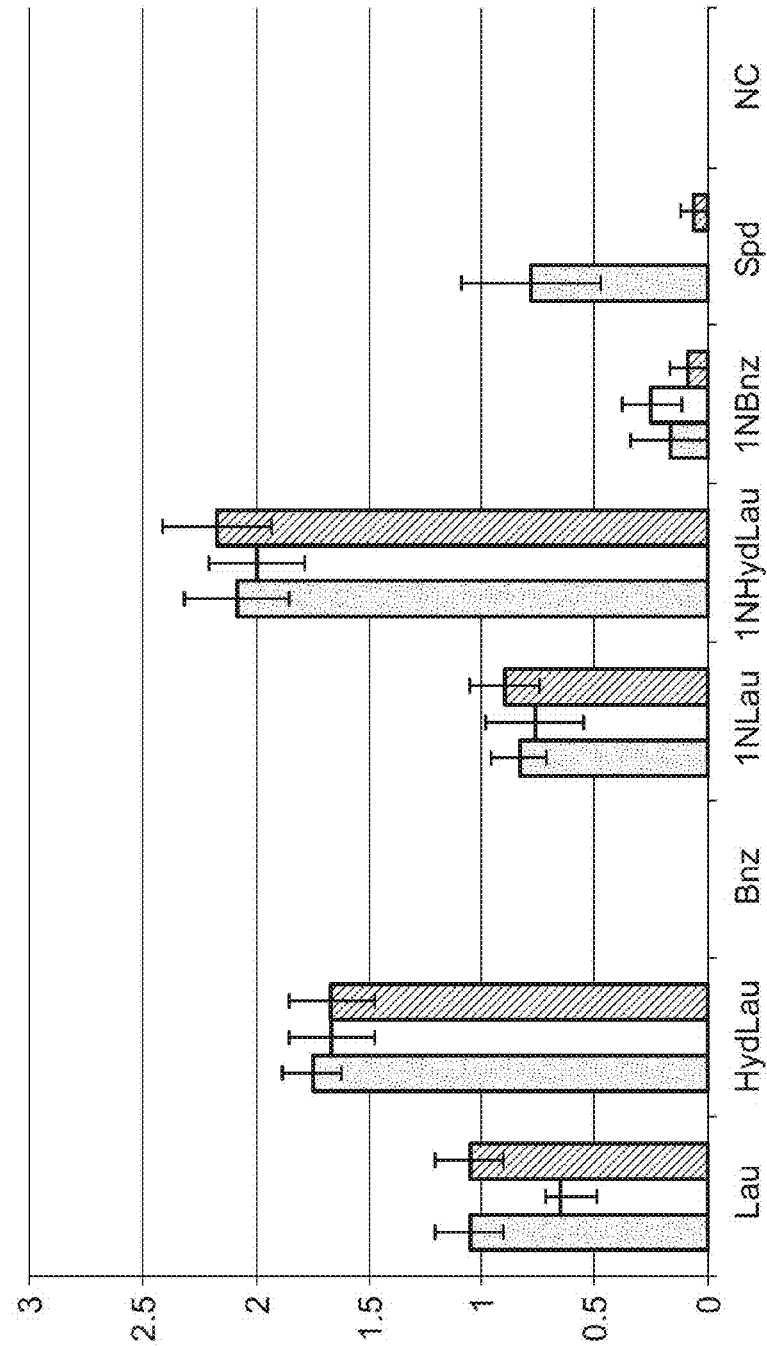
FIG. 12 shows severity of cell death induced by applying the compounds introduced with hydroxyl group into the lauroyl group. In the graph, HydLau denotes YIS12OH4N, and 1NhydLau denotes YIS12OH1N.
Figure 13A:
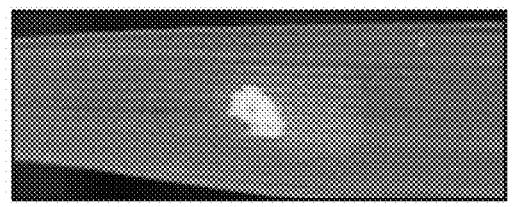
FIG. 13 shows cell death spots observed after applying the compounds introduced with hydroxyl group into the lauroyl group.
Figure 13B:
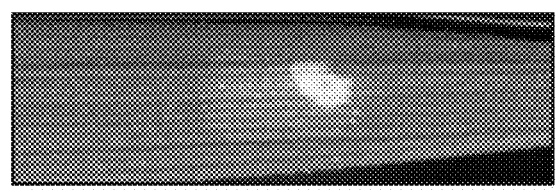

In the same manner as that of Example 4, formation of cell death spots and severity of cell death were examined by using YIS12OH1N and YIS12OH4N. The results of examination for severity of cell death are shown in FIG. 12, and those for formation of cell death spots are shown in FIG. 13. The severity of cell death was enhanced by each of the compounds introduced with one hydroxyl group at the terminal carbon atom of the lauroyl group (HydLau: YIS12OH4N, 1NHydLau: YIS12OH1N) compared with the compounds not introduced with hydroxyl group (Lau or $^1$N Lau).

Example 9

Figure 14:
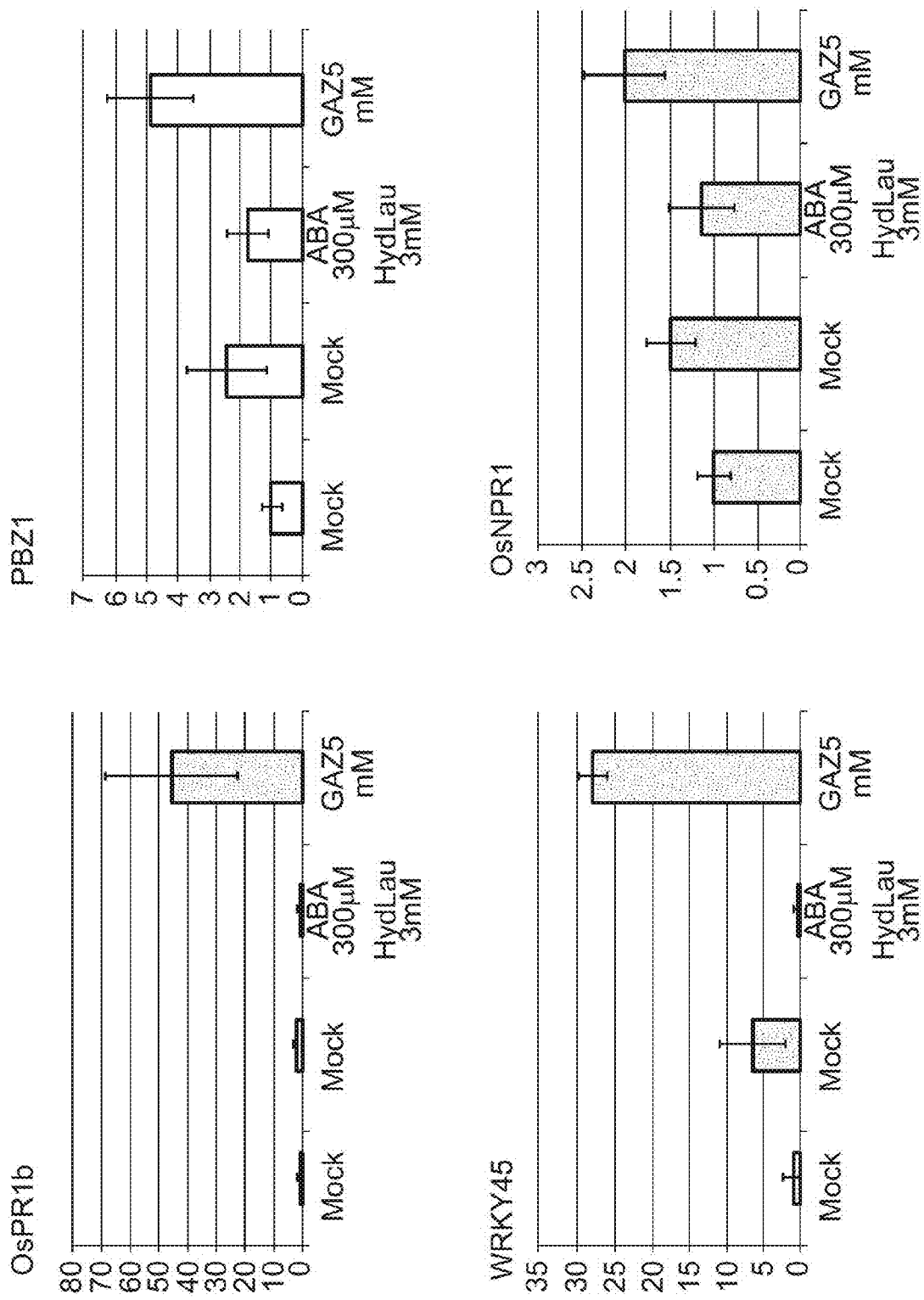
FIG. 14 shows results of examination for resistance related gene induction action of YIS12OH4N (HydLau, 3 mM) carried out in the presence of a polyamine oxygenase inhibitor, guazatine. In the graphs, Mock denotes the results obtained with a treatment using a solution not containing a test compound, and ABA denotes results obtained with a treatment using abscisic acid. ABA has been reported to show an inhibitory effect against disease damage resistance based on acquired systemic resistance, and it also had an inhibitory effect against disease damage resistance induced by the compound of the present invention.

In the same manner as that of Example 6, effect of YIS12OH4N (HydLau) at 3 mM on expression of rice plant disease damage resistance marker genes OsPR1b, PBZ1, WRKY45, and OsNPR1 was examined in the presence of 5 mM guazatine (GAZ), which is a polyamine oxygenase (PA) inhibitor. The results are shown in FIG. 14. In the presence of guazatine, the enhancement of expression of the rice plant disease damage resistance marker genes by YIS12OH4N (HydLau) was further promoted.

Example 10

Figure 15:
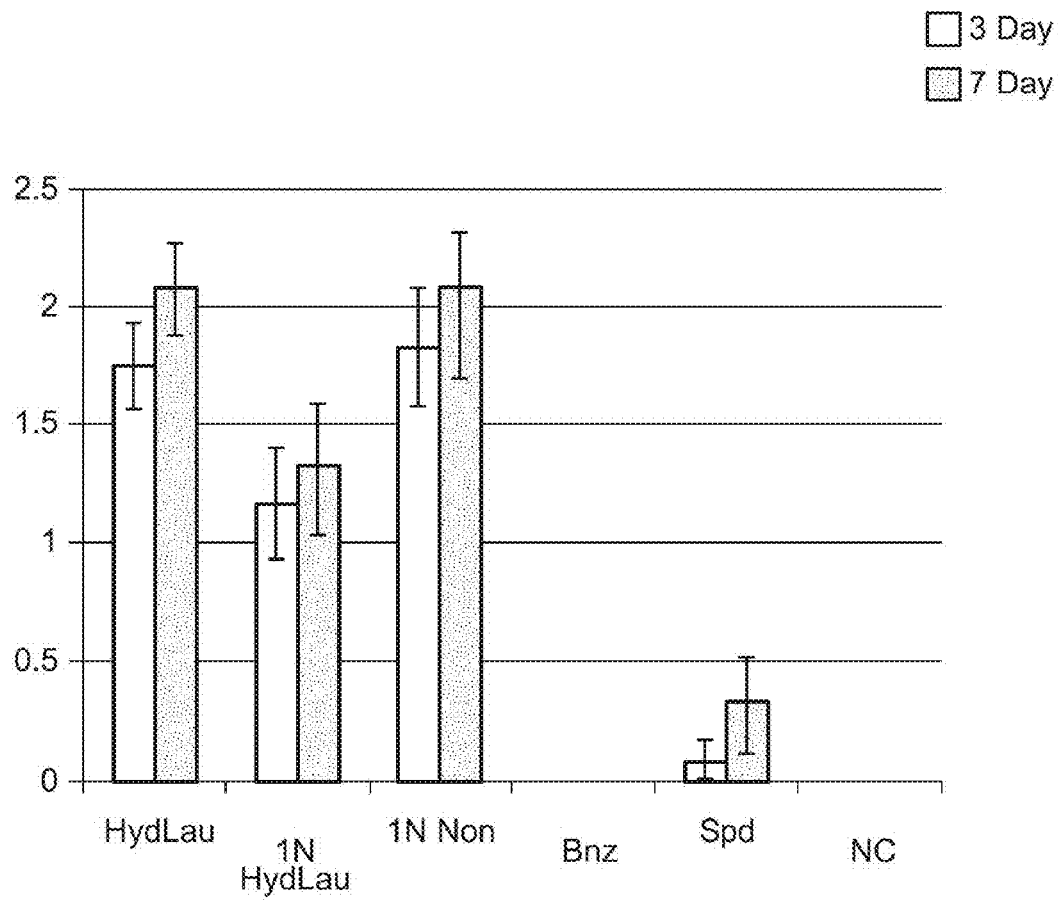
FIG. 15 shows severity of cell death induced by applying spermidine derivatives to *Arabidopsis thaliana*. Symbol "3d" denotes the results obtained after 3 days, and "7d" denotes the results obtained after 7 days.
Figure 16:
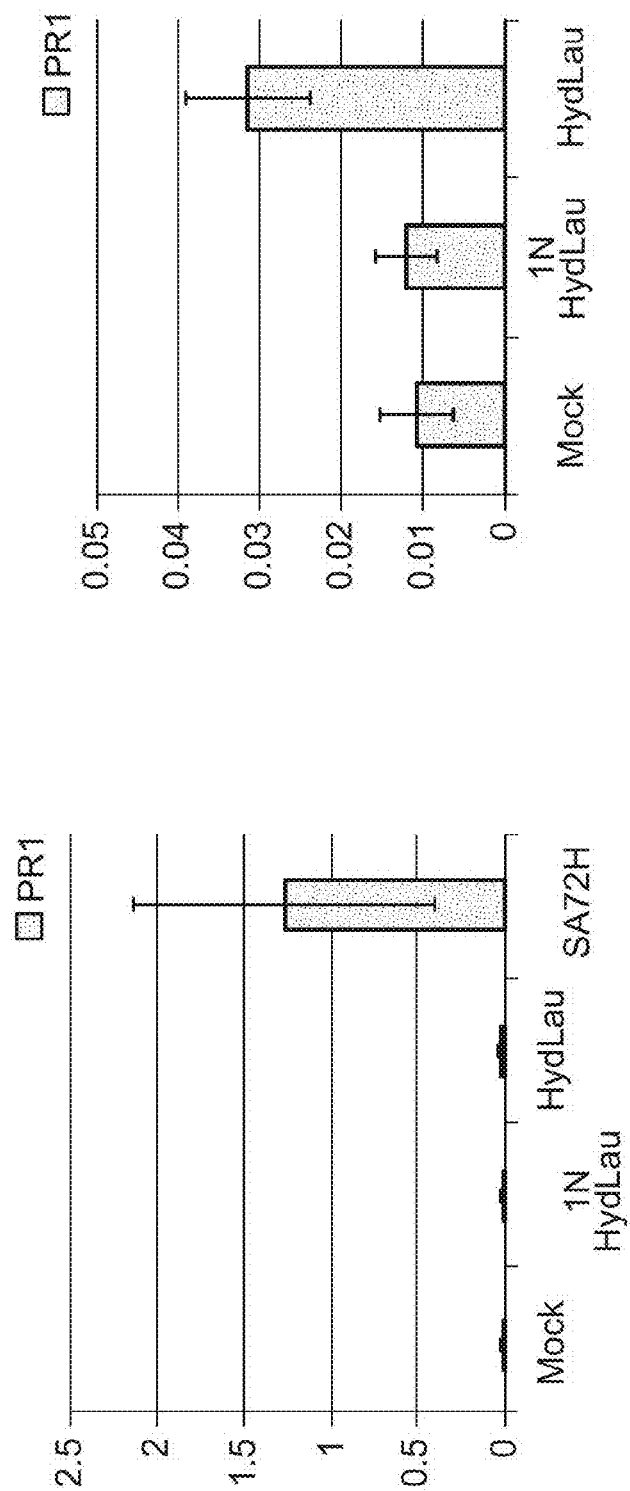
FIG. 16 shows results of examination on PR1 gene expression enhancing action of YIS12OH1N (1NHydLau) or YIS12OH4N (HydLau) carried out for *Arabidopsis thaliana*. The left graph shows the results obtained after 24 hours, and the right graph shows the results obtained after 72 hours.

In the same manner as that of Example 4, a dicotyledonous plant, *Arabidopsis thaliana*, was treated with YIS12OH1N (1NHydLau), YIS12OH4N (HydLau), $^1$N Non, Bnz, and spermidine (Spd), and cell death was observed by visual inspection. The results are shown in FIG. 15. 1NHydLau, HydLau, and 1N Non induced severe cell death also for *Arabidopsis thaliana*. The results of examination for PR1 gene expression enhancing action of YIS12OH1N (1NHydLau) and YIS12OH4N (HydLau) are shown in FIG. 16. After 24 hours and 72 hours, HydLau showed PR1 gene expression enhancing action about 3 times higher than that of 1NHydLau.

The entire disclosures of the references cited in the present specification are incorporated into the disclosure of the present specification by reference.

What is claimed is:

1. A compound of the following formula or a salt thereof:

$(R^3)NH-(CH_2)_4-N(R^1)-(CH_2)_3-NH(R^2)$ wherein $R^2$ is a linear alkanoyl group having 6 to 18 carbon atoms or a linear alkenoyl group having 6 to 18 carbon atoms, either of which may have 1 to 3 hydroxyl groups and/or 1 to 3 alkyl groups with 1 to 4 carbon atoms; $R^1$ is a hydrogen atom; and $R^3$ is a hydrogen atom.

2. The compound or a salt thereof according to claim 1, wherein $R^2$ is a linear alkanoyl group having 8 to 13 carbon atoms or a linear alkenoyl group having 8 to 13 carbon atoms, either of which may have 1 to 3 hydroxyl groups, $R^1$ is a hydrogen atom, and $R^3$ is a hydrogen atom.

3. The compound or a salt thereof according to claim 1, wherein $R^2$ is a linear alkanoyl group having 8 to 13 carbon atoms, which may have 1 to 3 hydroxyl groups, and $R^1$ is a hydrogen atom, and $R^3$ is a hydrogen atom.

4. The compound or a salt thereof according to claim 1, wherein $R^2$ is a linear alkanoyl group having 9 to 12 carbon atoms, and which may have 1 or 2 hydroxyl groups.

5. The compound or a salt thereof according to claim 1, wherein $R^2$ is a linear alkanoyl group having 9 to 12 carbon atoms and one hydroxyl group.

6. The compound or a salt thereof according to claim 1, wherein $R^2$ is a linear alkanoyl group having 9 to 12 carbon atoms and one hydroxyl group at the end.

7. A plant activator comprising the compound or a salt thereof according to claim 1 as an active ingredient.

8. The plant activator according to claim 7, which is used for control of disease damage of a plant.

9. A method for control of disease damage in a plant, which comprises applying the compound or a salt thereof according to claim 1 to the plant in an amount effective for the control.

* * * * *